United States Patent
Tieu

(10) Patent No.: US 9,242,070 B2
(45) Date of Patent: Jan. 26, 2016

(54) SYSTEM AND METHOD FOR LOCATING DETACHMENT ZONE OF A DETACHABLE IMPLANT

(75) Inventor: Tai D. Tieu, Fountain Valley, CA (US)

(73) Assignee: MicronVention, Inc., Tustin, CA (US)

( * ) Notice: Subject to any disclaimer, the term of this patent is extended or adjusted under 35 U.S.C. 154(b) by 1506 days.

(21) Appl. No.: 12/340,546

(22) Filed: Dec. 19, 2008

(65) Prior Publication Data
US 2009/0163780 A1   Jun. 25, 2009

Related U.S. Application Data

(60) Provisional application No. 61/016,154, filed on Dec. 21, 2007.

(51) Int. Cl.
*A61M 29/00* (2006.01)
*A61B 5/00* (2006.01)
(Continued)

(52) U.S. Cl.
CPC ........ *A61M 25/0082* (2013.01); *A61B 17/1214* (2013.01); *A61B 17/12022* (2013.01); *A61B 17/12109* (2013.01); *A61B 17/12113* (2013.01); *A61B 17/12122* (2013.01); *A61B 17/12154* (2013.01); *A61F 2/95* (2013.01); *A61M 25/0108* (2013.01); *A61B 2017/12068* (2013.01); *A61F 2/966* (2013.01); *A61F 2002/30668* (2013.01); *A61F 2002/9505* (2013.01); *A61F 2250/0001* (2013.01); *A61M 25/0068* (2013.01); *A61M 2025/0042* (2013.01); *A61M 2025/0681* (2013.01); *A61M 2205/3331* (2013.01); *A61M 2205/3368* (2013.01); *A61M 2205/3375* (2013.01); *A61M 2205/3653* (2013.01)

(58) Field of Classification Search
CPC ..................... A61M 25/0108; A61M 2205/18; A61B 17/12022; A61B 17/12113; A61B 2017/12068
USPC ........................... 606/200, 108; 600/301, 424
See application file for complete search history.

(56) References Cited

U.S. PATENT DOCUMENTS 4,346,712 A   8/1982   Handa et al.
4,364,392 A   12/1982   Strother et al.
(Continued)

FOREIGN PATENT DOCUMENTS

AU   2005/276980 B2   3/2006
CA   2493016 A1   2/2004
(Continued)

OTHER PUBLICATIONS

United States Patent and Trademark Office, Notice of Allowance mailed Feb. 15, 2012 in U.S. Appl. No. 12/340,616, 17 pages.
(Continued)

*Primary Examiner* — Katherine Rodjom
(74) *Attorney, Agent, or Firm* — Inskeep IP Group, Inc.

(57) ABSTRACT

A system and method for quickly detaching an implant and for locating the detachment zone of a detachable implant. A sensor determines a sudden change in the local environment as the sensor passes from within a microcatheter to being exposed to the vasculature. The sensor may be a temperature sensor, ultrasonic sensor, pressure sensor or the like. If the detachable implant assembly uses a heater coil to detach the implant, the heater coil may be used as a sensor. Additionally, the implant itself may be used as a sensor if a change in electrical resistance is detectable as the implant exits the microcatheter and changes shape.

6 Claims, 6 Drawing Sheets

(51) Int. Cl.
*A61M 25/00* (2006.01)
*A61B 17/12* (2006.01)
*A61F 2/95* (2013.01)
*A61M 25/01* (2006.01)
A61F 2/966 (2013.01)
A61F 2/30 (2006.01)
A61M 25/06 (2006.01)

(56) References Cited

U.S. PATENT DOCUMENTS

| | | |
|---|---|---|
| 4,402,319 A | 9/1983 | Handa et al. |
| 4,512,338 A | 4/1985 | Balko et al. |
| 4,545,367 A | 10/1985 | Tucci |
| 4,551,132 A | 11/1985 | Pasztor et al. |
| 4,638,803 A | 1/1987 | Rand |
| RE32,348 E | 2/1987 | Pevsner |
| 4,735,201 A | 4/1988 | O'Reilly |
| 4,795,741 A | 1/1989 | Leshchiner et al. |
| 4,819,637 A | 4/1989 | Dormandy, Jr. et al. |
| 4,944,746 A | 7/1990 | Iwata et al. |
| 4,994,069 A | 2/1991 | Ritchart et al. |
| 5,001,009 A | 3/1991 | Whitbourne |
| 5,108,407 A | 4/1992 | Geremia et al. |
| 5,122,136 A | 6/1992 | Guglielmi et al. |
| 5,133,731 A | 7/1992 | Butler et al. |
| 5,147,370 A | 9/1992 | McNamara et al. |
| 5,163,952 A | 11/1992 | Froix |
| 5,167,624 A | 12/1992 | Butler et al. |
| 5,217,484 A | 6/1993 | Marks |
| 5,226,911 A | 7/1993 | Chee et al. |
| 5,250,071 A | 10/1993 | Palermo |
| 5,256,146 A | 10/1993 | Ensminger et al. |
| 5,258,042 A | 11/1993 | Mehta |
| 5,261,916 A | 11/1993 | Engelson |
| 5,269,030 A | 12/1993 | Pahno et al. |
| 5,304,194 A | 4/1994 | Chee et al. |
| 5,311,027 A | 5/1994 | Schuetz |
| 5,312,415 A | 5/1994 | Palermo |
| 5,331,027 A | 7/1994 | Whitbourne |
| 5,334,201 A | 8/1994 | Cowan |
| 5,334,210 A | 8/1994 | Gianturco |
| 5,350,397 A | 9/1994 | Palermo et al. |
| 5,354,295 A | 10/1994 | Guglielmi et al. |
| 5,382,259 A | 1/1995 | Phelps et al. |
| 5,382,260 A | 1/1995 | Dormandy, Jr. et al. |
| 5,383,887 A | 1/1995 | Nadal |
| 5,423,777 A | 6/1995 | Tajiri et al. |
| 5,423,829 A | 6/1995 | Pham et al. |
| 5,423,849 A | 6/1995 | Engelson et al. |
| 5,443,454 A | 8/1995 | Tanabe et al. |
| 5,443,478 A | 8/1995 | Purdy |
| 5,443,495 A | 8/1995 | Buscemi et al. |
| 5,469,867 A | 11/1995 | Schmitt |
| 5,470,338 A | 11/1995 | Whitfield et al. |
| 5,476,472 A | 12/1995 | Dormandy |
| 5,498,227 A | 3/1996 | Mawad |
| 5,498,250 A | 3/1996 | Prather |
| 5,522,836 A | 6/1996 | Palermo |
| 5,525,334 A | 6/1996 | Ito et al. |
| 5,529,653 A | 6/1996 | Glastra |
| 5,536,274 A | 7/1996 | Neuss |
| 5,540,680 A | 7/1996 | Guglielmi et al. |
| 5,569,245 A | 10/1996 | Guglielmi et al. |
| 5,578,074 A | 11/1996 | Mirigian |
| 5,580,568 A | 12/1996 | Greff et al. |
| 5,582,619 A | 12/1996 | Ken |
| 5,593,412 A | 1/1997 | Martinez et al. |
| 5,601,600 A | 2/1997 | Ton |
| 5,609,608 A | 3/1997 | Benett et al. |
| 5,612,050 A | 3/1997 | Rowe et al. |
| 5,614,204 A | 3/1997 | Cochrum |
| 5,624,449 A | 4/1997 | Pham et al. |
| 5,624,461 A | 4/1997 | Mariant |
| 5,624,685 A | 4/1997 | Takahashi et al. |
| 5,634,936 A | 6/1997 | Linden et al. |
| 5,639,277 A | 6/1997 | Mariant et al. |
| 5,645,558 A | 7/1997 | Horton |
| 5,658,308 A | 8/1997 | Snyder |
| 5,667,767 A | 9/1997 | Greff et al. |
| 5,669,931 A | 9/1997 | Kupiecki et al. |
| 5,690,667 A | 11/1997 | Gia |
| 5,690,671 A | 11/1997 | McGurk et al. |
| 5,700,258 A | 12/1997 | Mirigian et al. |
| 5,702,361 A | 12/1997 | Evans et al. |
| 5,718,711 A | 2/1998 | Berenstein et al. |
| 5,722,989 A | 3/1998 | Fitch et al. |
| 5,725,568 A | 3/1998 | Hastings |
| 5,733,329 A | 3/1998 | Wallace et al. |
| 5,743,905 A | 4/1998 | Eder et al. |
| 5,749,891 A | 5/1998 | Ken et al. |
| 5,749,894 A | 5/1998 | Engelson |
| 5,749,921 A | 5/1998 | Lenker et al. |
| 5,750,585 A | 5/1998 | Park et al. |
| 5,759,161 A | 6/1998 | Ogawa et al. |
| 5,766,204 A | 6/1998 | Porter et al. |
| 5,766,219 A | 6/1998 | Horton |
| 5,792,154 A | 8/1998 | Doan et al. |
| 5,800,454 A | 9/1998 | Jacobsen et al. |
| 5,800,455 A | 9/1998 | Palermo et al. |
| 5,814,062 A | 9/1998 | Sepetka et al. |
| 5,823,198 A | 10/1998 | Jones et al. |
| 5,830,178 A | 11/1998 | Jones et al. |
| 5,830,230 A | 11/1998 | Berryman et al. |
| 5,846,210 A | 12/1998 | Ogawa et al. |
| 5,846,247 A | 12/1998 | Unsworth et al. |
| 5,851,206 A | 12/1998 | Guglielmi et al. |
| 5,851,508 A | 12/1998 | Greff et al. |
| 5,853,418 A | 12/1998 | Ken et al. |
| 5,891,058 A | 4/1999 | Taki et al. |
| 5,891,130 A | 4/1999 | Palermo et al. |
| 5,895,385 A | 4/1999 | Guglielmi et al. |
| 5,902,254 A | 5/1999 | Magram |
| 5,911,737 A | 6/1999 | Lee et al. |
| 5,925,037 A | 7/1999 | Guglielmi et al. |
| 5,925,059 A | 7/1999 | Palermo et al. |
| 5,925,061 A | 7/1999 | Ogi et al. |
| 5,941,888 A | 8/1999 | Wallace et al. |
| 5,944,733 A | 8/1999 | Engelson |
| 5,947,963 A | 9/1999 | Guglielmi |
| 5,964,771 A | 10/1999 | Beyar et al. |
| 5,964,797 A | 10/1999 | Ho |
| 5,976,126 A | 11/1999 | Guglielmi et al. |
| 5,976,131 A | 11/1999 | Guglielmi et al. |
| 5,984,929 A | 11/1999 | Brodersen et al. |
| 6,010,498 A | 1/2000 | Guglielmi |
| 6,013,084 A | 1/2000 | Ken et al. |
| 6,015,424 A | 1/2000 | Rosenbluth et al. |
| 6,033,423 A | 3/2000 | Ken et al. |
| 6,048,338 A | 4/2000 | Larson et al. |
| 6,053,873 A | 4/2000 | Govari et al. |
| 6,056,759 A | 5/2000 | Fiedler |
| 6,059,815 A | 5/2000 | Lee et al. |
| 6,063,070 A | 5/2000 | Eder |
| 6,063,100 A | 5/2000 | Diaz et al. |
| 6,066,133 A | 5/2000 | Guglielmi et al. |
| 6,068,644 A | 5/2000 | Lulo et al. |
| 6,083,220 A | 7/2000 | Guglielmi et al. |
| 6,086,599 A | 7/2000 | Lee et al. |
| 6,091,980 A * | 7/2000 | Squire et al. ............... 600/381 |
| 6,102,932 A | 8/2000 | Kurz |
| 6,117,142 A | 9/2000 | Goodson et al. |
| 6,159,206 A * | 12/2000 | Ogawa ............ A61B 17/12022 606/29 |
| 6,165,178 A | 12/2000 | Bashiri et al. |
| 6,193,728 B1 | 2/2001 | Ken et al. |
| 6,221,066 B1 | 4/2001 | Ferrera et al. |
| 6,224,609 B1 | 5/2001 | Ressemann et al. |
| 6,238,403 B1 | 5/2001 | Greene, Jr. et al. |
| 6,238,415 B1 | 5/2001 | Sepetka et al. |
| 6,277,126 B1 | 8/2001 | Barry et al. |
| 6,293,960 B1 | 9/2001 | Ken |
| 6,296,622 B1 | 10/2001 | Kurz et al. |
| 6,299,619 B1 | 10/2001 | Greene, Jr. et al. |

(56) References Cited

U.S. PATENT DOCUMENTS

| | | | |
|---|---|---|---|
| 6,319,267 B1 | 11/2001 | Kurz | |
| 6,338,657 B1 | 1/2002 | Harper et al. | |
| 6,361,547 B1 | 3/2002 | Hieshima | |
| 6,371,979 B1 | 4/2002 | Beyar et al. | |
| 6,375,668 B1 | 4/2002 | Gifford et al. | |
| 6,375,669 B1 | 4/2002 | Rosenbluth et al. | |
| 6,383,204 B1 | 5/2002 | Ferrera et al. | |
| 6,425,893 B1 | 7/2002 | Guglielmi | |
| 6,428,557 B1 | 8/2002 | Hilaire | |
| 6,440,098 B1 | 8/2002 | Luscher | |
| 6,447,522 B2 | 9/2002 | Gambale et al. | |
| 6,478,773 B1 | 11/2002 | Gandhi et al. | |
| 6,494,884 B2 | 12/2002 | Gifford, III et al. | |
| 6,500,149 B2 | 12/2002 | Gandhi et al. | |
| 6,514,264 B1 | 2/2003 | Naglreiter | |
| 6,526,979 B1 | 3/2003 | Nikolchev et al. | |
| 6,544,225 B1 | 4/2003 | Lulo et al. | |
| 6,554,849 B1 | 4/2003 | Jones et al. | |
| 6,602,261 B2 | 8/2003 | Greene, Jr. et al. | |
| 6,602,269 B2 | 8/2003 | Wallace et al. | |
| 6,607,538 B1 | 8/2003 | Ferrera et al. | |
| 6,610,046 B1 | 8/2003 | Usami et al. | |
| 6,634,361 B1 | 10/2003 | Nikolchev et al. | |
| 6,645,240 B2 | 11/2003 | Yee | |
| 6,656,173 B1 | 12/2003 | Palermo | |
| 6,684,884 B2 | 2/2004 | Nikolchev et al. | |
| 6,689,141 B2 | 2/2004 | Ferrera et al. | |
| 6,705,323 B1 | 3/2004 | Nikolchev et al. | |
| 6,716,238 B2 | 4/2004 | Elliott | |
| 6,740,073 B1 | 5/2004 | Saville | |
| 6,743,236 B2 | 6/2004 | Barry et al. | |
| 6,743,251 B1 | 6/2004 | Eder | |
| 6,807,446 B2 | 10/2004 | Fenn et al. | |
| 6,849,081 B2 | 2/2005 | Sepetka et al. | |
| 6,849,087 B1 | 2/2005 | Chuter | |
| 6,855,125 B2 | 2/2005 | Shanley | |
| 6,905,503 B2 | 6/2005 | Gifford, III et al. | |
| 6,953,465 B2 | 10/2005 | Dieck et al. | |
| 6,953,473 B2 | 10/2005 | Porter | |
| 6,958,068 B2 | 10/2005 | Hieshima | |
| 6,964,671 B2 | 11/2005 | Cheng et al. | |
| 6,966,892 B2 | 11/2005 | Gandhi et al. | |
| 6,989,020 B2 | 1/2006 | Jones et al. | |
| 7,001,422 B2 | 2/2006 | Escamilla et al. | |
| 7,014,645 B2 | 3/2006 | Greene, Jr. et al. | |
| 7,048,719 B1 | 5/2006 | Monetti | |
| 7,063,671 B2 | 6/2006 | Couvillon, Jr. | |
| 7,063,707 B2 | 6/2006 | Bose et al. | |
| 7,066,904 B2 | 6/2006 | Rosenthal et al. | |
| 7,070,609 B2 | 7/2006 | West | |
| 7,108,708 B2 | 9/2006 | Cheng et al. | |
| 7,137,990 B2 | 11/2006 | Hebert et al. | |
| 7,147,618 B2 | 12/2006 | Kurz | |
| 7,166,122 B2 | 1/2007 | Aganon et al. | |
| 7,179,276 B2 | 2/2007 | Barry et al. | |
| 7,182,774 B2 | 2/2007 | Barry et al. | |
| 7,198,613 B2 | 4/2007 | Gandhi et al. | |
| 7,201,768 B2 | 4/2007 | Diaz et al. | |
| 7,208,003 B2 | 4/2007 | Davis et al. | |
| 7,238,194 B2 | 7/2007 | Monstdt et al. | |
| 7,255,707 B2 | 8/2007 | Ramzipoor et al. | |
| 7,264,628 B2 | 9/2007 | Jones et al. | |
| 7,270,674 B2 | 9/2007 | Jones et al. | |
| 7,309,345 B2 | 12/2007 | Wallace | |
| 7,323,000 B2 | 1/2008 | Monstdt et al. | |
| 7,344,558 B2 | 3/2008 | Lorenzo et al. | |
| 7,351,254 B2 | 4/2008 | Magers | |
| 7,357,809 B2 | 4/2008 | Jones et al. | |
| 7,367,987 B2 | 5/2008 | Balgobin et al. | |
| 7,371,251 B2 | 5/2008 | Mitelberg et al. | |
| 7,371,252 B2 | 5/2008 | Balgobin et al. | |
| 7,377,932 B2 | 5/2008 | Mitelberg et al. | |
| 7,513,878 B2 | 4/2009 | Hamilton | |
| 7,553,321 B2 | 6/2009 | Litzenberg et al. | |
| 7,575,582 B2 | 8/2009 | Gandhi et al. | |
| 7,578,826 B2 | 8/2009 | Gandhi et al. | |
| 7,582,101 B2 | 9/2009 | Jones et al. | |
| 7,591,833 B2 | 9/2009 | Jones et al. | |
| 7,608,089 B2 | 10/2009 | Wallace et al. | |
| 7,628,797 B2 | 12/2009 | Tieu et al. | |
| 7,651,513 B2 | 1/2010 | Teoh et al. | |
| 7,691,118 B2 | 4/2010 | Gorospe | |
| 7,708,754 B2 | 5/2010 | Balgobin et al. | |
| 7,708,755 B2 | 5/2010 | Davis, III et al. | |
| 7,740,637 B2 | 6/2010 | Gandhi et al. | |
| 7,771,451 B2 | 8/2010 | Ramzipoor | |
| 7,776,054 B2 | 8/2010 | Gandhi et al. | |
| 7,780,680 B2 | 8/2010 | Gandhi et al. | |
| 7,789,891 B2 | 9/2010 | Wallace | |
| 2001/0029352 A1 | 10/2001 | Gandhi et al. | |
| 2002/0046756 A1* | 4/2002 | Laizzo et al. | 128/899 |
| 2002/0091380 A1 | 7/2002 | Wheelock et al. | |
| 2002/0107534 A1 | 8/2002 | Schaefer et al. | |
| 2002/0188341 A1 | 12/2002 | Elliott | |
| 2003/0023262 A1 | 1/2003 | Welch | |
| 2003/0045901 A1 | 3/2003 | Opolski | |
| 2003/0069539 A1 | 4/2003 | Gandhi et al. | |
| 2003/0125790 A1 | 7/2003 | Fastovsky et al. | |
| 2004/0002731 A1 | 1/2004 | Aganon et al. | |
| 2004/0002733 A1 | 1/2004 | Teoh | |
| 2004/0034363 A1 | 2/2004 | Wilson et al. | |
| 2004/0044385 A1 | 3/2004 | Fenn et al. | |
| 2004/0204701 A1 | 10/2004 | Cox et al. | |
| 2005/0021023 A1* | 1/2005 | Guglielmi et al. | 606/41 |
| 2005/0043755 A1* | 2/2005 | Wilson et al. | 606/200 |
| 2005/0118865 A1 | 6/2005 | Henningsen | |
| 2005/0131523 A1 | 6/2005 | Bashiri et al. | |
| 2005/0149108 A1 | 7/2005 | Cox | |
| 2005/0154417 A1 | 7/2005 | Sepetka et al. | |
| 2005/0171572 A1 | 8/2005 | Martinez | |
| 2005/0222580 A1 | 10/2005 | Gifford, III et al. | |
| 2005/0283182 A1 | 12/2005 | Pierce et al. | |
| 2006/0025801 A1 | 2/2006 | Lulo et al. | |
| 2006/0025803 A1 | 2/2006 | Mitelberg et al. | |
| 2006/0036280 A1 | 2/2006 | French et al. | |
| 2006/0052815 A1* | 3/2006 | Fitz et al. | 606/200 |
| 2006/0079923 A1 | 4/2006 | Chhabra et al. | |
| 2006/0116708 A1 | 6/2006 | Ogawa et al. | |
| 2006/0135986 A1 | 6/2006 | Wallace et al. | |
| 2006/0173488 A1 | 8/2006 | Takeuchi et al. | |
| 2006/0184092 A1 | 8/2006 | Atanasoska et al. | |
| 2006/0200192 A1 | 9/2006 | Fitz et al. | |
| 2006/0241682 A1 | 10/2006 | Kurz | |
| 2006/0241684 A1 | 10/2006 | Wilson et al. | |
| 2006/0241685 A1 | 10/2006 | Wilson et al. | |
| 2006/0253023 A1 | 11/2006 | Lewis et al. | |
| 2006/0253149 A1 | 11/2006 | Gandhi et al. | |
| 2006/0271098 A1 | 11/2006 | Peacock, III | |
| 2006/0271099 A1 | 11/2006 | Marks et al. | |
| 2006/0276826 A1 | 12/2006 | Mitelberg et al. | |
| 2007/0055302 A1 | 3/2007 | Henry et al. | |
| 2007/0100419 A1 | 5/2007 | Licata et al. | |
| 2007/0104752 A1 | 5/2007 | Lee et al. | |
| 2007/0167911 A1 | 7/2007 | Gandhi et al. | |
| 2007/0185443 A1 | 8/2007 | Euteneuer et al. | |
| 2007/0185457 A1 | 8/2007 | Euteneuer et al. | |
| 2007/0191879 A1 | 8/2007 | Gandhi et al. | |
| 2007/0208276 A1 | 9/2007 | Kornkven Volk et al. | |
| 2007/0239141 A1 | 10/2007 | Hartley et al. | |
| 2007/0239193 A1 | 10/2007 | Simon et al. | |
| 2008/0103585 A1 | 5/2008 | Monstdt et al. | |
| 2008/0119887 A1 | 5/2008 | Que et al. | |
| 2008/0125855 A1 | 5/2008 | Henkes et al. | |
| 2008/0133028 A1 | 6/2008 | Wilson et al. | |
| 2008/0140111 A1 | 6/2008 | Wilson et al. | |
| 2008/0140178 A1 | 6/2008 | Rasmussen et al. | |
| 2008/0147201 A1 | 6/2008 | Wilson et al. | |
| 2008/0172119 A1* | 7/2008 | Yamasaki et al. | 623/1.11 |
| 2008/0221554 A1 | 9/2008 | O'Connor et al. | |
| 2008/0283066 A1 | 11/2008 | Delgado et al. | |
| 2008/0287982 A1 | 11/2008 | Harreld | |
| 2009/0018653 A1 | 1/2009 | Bashiri et al. | |
| 2009/0054905 A1 | 2/2009 | Levy | |
| 2009/0062726 A1 | 3/2009 | Ford et al. | |

(56) References Cited

U.S. PATENT DOCUMENTS

| | | |
|---|---|---|
| 2009/0076540 A1 | 3/2009 | Marks et al. |
| 2009/0099592 A1 | 4/2009 | Buiser et al. |
| 2009/0138036 A1 | 5/2009 | Nardone et al. |
| 2009/0143786 A1 | 6/2009 | Bashiri et al. |
| 2009/0163780 A1 | 6/2009 | Tieu |
| 2009/0163986 A1 | 6/2009 | Tieu et al. |
| 2009/0177261 A1 | 7/2009 | Teoh et al. |
| 2009/0270901 A1 | 10/2009 | Kelleher et al. |
| 2009/0270903 A1 | 10/2009 | Litzenberg et al. |
| 2009/0275971 A1 | 11/2009 | Kelleher et al. |
| 2009/0299275 A1 | 12/2009 | Gandhi et al. |
| 2009/0318892 A1 | 12/2009 | Aboytes et al. |
| 2010/0004731 A1 | 1/2010 | Gandhi et al. |
| 2010/0042133 A1 | 2/2010 | Ramzipoor et al. |
| 2010/0069838 A1 | 3/2010 | Weber et al. |
| 2010/0094395 A1 | 4/2010 | Kellett |
| 2010/0106162 A1 | 4/2010 | Jaeger et al. |
| 2010/0152650 A1 | 6/2010 | Schrodt |
| 2010/0152828 A1 | 6/2010 | Pakbaz et al. |
| 2010/0160944 A1 | 6/2010 | Teoh et al. |
| 2010/0160953 A1 | 6/2010 | Ngo et al. |
| 2010/0234872 A1 | 9/2010 | Guo et al. |
| 2010/0249823 A1 | 9/2010 | Gandhi et al. |
| 2010/0256666 A1 | 10/2010 | Chen et al. |
| 2010/0268158 A1 | 10/2010 | Porter |
| 2010/0268201 A1 | 10/2010 | Tieu et al. |
| 2010/0268204 A1 | 10/2010 | Tieu et al. |
| 2010/0268252 A1 | 10/2010 | Chen et al. |

FOREIGN PATENT DOCUMENTS

| | | |
|---|---|---|
| CN | 101589972 A | 12/2009 |
| CN | 20110506 A | 5/2011 |
| EP | 0 547 530 A1 | 6/1993 |
| EP | 0 707 830 A1 | 4/1996 |
| EP | 0 719 522 A1 | 7/1996 |
| EP | 0 941 703 A1 | 9/1999 |
| EP | 0 941 704 A1 | 9/1999 |
| EP | 0 948 935 A1 | 10/1999 |
| EP | 0 992 220 A1 | 10/1999 |
| EP | 1 010 396 A1 | 6/2000 |
| EP | 1 073 377 A1 | 2/2001 |
| EP | 2 319 455 A2 | 5/2001 |
| EP | 0 842 010 B1 | 2/2003 |
| EP | 1 188 413 A3 | 7/2003 |
| EP | 0 830 873 B1 | 4/2004 |
| EP | 1 531 461 A | 3/2005 |
| EP | 1 538 997 B1 | 6/2005 |
| EP | 1 266 629 B1 | 11/2006 |
| EP | 1 738 698 A2 | 1/2007 |
| EP | 1 791 590 A | 6/2007 |
| EP | 1 797 832 A1 | 6/2007 |
| EP | 1 797 833 A1 | 6/2007 |
| EP | 1 621 150 B1 | 9/2007 |
| EP | 1 621 148 B1 | 10/2007 |
| EP | 1 339 328 B1 | 2/2008 |
| EP | 1 621 149 B1 | 2/2008 |
| EP | 1 889 577 A1 | 2/2008 |
| EP | 1 738 694 B1 | 7/2008 |
| EP | 1 743 600 B1 | 7/2008 |
| EP | 1 738 696 B1 | 8/2008 |
| EP | 1 255 492 B1 | 10/2008 |
| EP | 1 792 576 B1 | 10/2008 |
| EP | 1 795 133 B1 | 10/2008 |
| EP | 1 255 493 B1 | 11/2008 |
| EP | 1 738 693 B1 | 11/2008 |
| EP | 1 992 308 A2 | 11/2008 |
| EP | 1 813 196 B1 | 12/2008 |
| EP | 1 120 088 B1 | 4/2009 |
| EP | 1 825 823 B1 | 6/2009 |
| EP | 1 738 697 B1 | 4/2010 |
| EP | 1 792 575 B1 | 6/2010 |
| EP | 2 131 754 B1 | 6/2010 |
| EP | 2 231 030 A | 9/2010 |
| EP | 2 234 562 A | 10/2010 |
| EP | 1 985 240 B1 | 2/2011 |
| EP | 1 886 632 B1 | 4/2011 |
| EP | 1 813 213 B1 | 12/2011 |
| EP | 2 111 828 B1 | 2/2012 |
| JP | 52141092 A | 11/1977 |
| JP | 56043962 A | 4/1981 |
| JP | 01-238874 A | 9/1989 |
| JP | 5158069 A | 6/1992 |
| JP | 07-265431 A | 10/1995 |
| JP | H08506033 A | 7/1996 |
| JP | 2008-250576 A | 4/1998 |
| JP | 2003-521991 A | 7/2003 |
| JP | 2005-524479 A | 8/2005 |
| JP | 2008-510594 A | 4/2008 |
| JP | 2011-507636 A | 3/2011 |
| JP | 2011-507638 A | 3/2011 |
| WO | WO 91/13592 A1 | 9/1991 |
| WO | WO 94/06503 A1 | 3/1994 |
| WO | WO 94/10936 A1 | 5/1994 |
| WO | WO 95/07667 A1 | 3/1995 |
| WO | WO 95/23558 A1 | 9/1995 |
| WO | WO 95/27443 A1 | 10/1995 |
| WO | WO 96/00034 A1 | 1/1996 |
| WO | WO 96/00104 A1 | 1/1996 |
| WO | WO 97/26939 A1 | 7/1997 |
| WO | WO 97/27888 A1 | 8/1997 |
| WO | WO 98/29042 A1 | 7/1998 |
| WO | WO 98/37816 A1 | 9/1998 |
| WO | WO 98/40033 A3 | 9/1998 |
| WO | WO 99/02094 A1 | 1/1999 |
| WO | WO 99/06097 A1 | 2/1999 |
| WO | WO 99/09894 A1 | 3/1999 |
| WO | WO 99/29260 A2 | 6/1999 |
| WO | WO 99/40852 A1 | 8/1999 |
| WO | WO 99/42059 A2 | 8/1999 |
| WO | WO 99/55239 A1 | 11/1999 |
| WO | WO 00/12031 A1 | 3/2000 |
| WO | WO 00/21443 A1 | 4/2000 |
| WO | WO 00/53105 A1 | 9/2000 |
| WO | WO 00/72781 A2 | 12/2000 |
| WO | WO 01/58366 A1 | 8/2001 |
| WO | WO 02/32326 A2 | 4/2002 |
| WO | WO 03/094751 A1 | 11/2003 |
| WO | WO 2005/035020 A2 | 4/2005 |
| WO | WO 2005/077281 A1 | 8/2005 |
| WO | WO 2005/113035 A3 | 12/2005 |
| WO | WO 2006/024040 A2 | 3/2006 |
| WO | WO 2006/047748 A2 | 5/2006 |
| WO | WO 2006/069123 A1 | 6/2006 |
| WO | WO 2006/081448 A1 | 8/2006 |
| WO | WO 2006/104881 A2 | 10/2006 |
| WO | WO 2006/114325 A2 | 11/2006 |
| WO | WO 2006/130743 A1 | 12/2006 |
| WO | WO 2007/041407 A1 | 4/2007 |
| WO | WO 2007/053568 A1 | 5/2007 |
| WO | WO 2007/070788 A2 | 6/2007 |
| WO | WO 2007/070792 A2 | 6/2007 |
| WO | WO 2007/070793 A2 | 6/2007 |
| WO | WO 2007/070797 A2 | 6/2007 |
| WO | WO 2007/118015 A2 | 10/2007 |
| WO | WO 2007/121405 A2 | 10/2007 |
| WO | WO 2007/123657 A2 | 11/2007 |
| WO | WO 2008/064205 A2 | 5/2008 |
| WO | WO 2008/064206 A2 | 5/2008 |
| WO | WO 2008/064209 A1 | 5/2008 |
| WO | WO 2008/066923 A2 | 6/2008 |
| WO | WO 2008/085606 A1 | 7/2008 |
| WO | WO 2008/109394 A2 | 9/2008 |
| WO | WO 2008/115544 A2 | 9/2008 |
| WO | WO 2009/012057 A2 | 1/2009 |
| WO | WO 2009/014883 A1 | 1/2009 |
| WO | WO 2009/073398 A1 | 6/2009 |
| WO | WO 2009/082716 A1 | 7/2009 |
| WO | WO 2009/086214 A1 | 7/2009 |
| WO | WO 2009/088969 A2 | 7/2009 |
| WO | WO 2009/154844 A1 | 12/2009 |
| WO | WO 2010/030348 A1 | 3/2010 |
| WO | WO 2010/045079 A1 | 4/2010 |

(56) References Cited

FOREIGN PATENT DOCUMENTS

| WO | WO 2010/104955 A1 | 9/2010 |
|----|-------------------|--------|
| WO | WO 2010/117883 A1 | 10/2010 |
| WO | WO 2010/120653 A1 | 10/2010 |
| WO | WO 2010/120694 A1 | 10/2010 |
| WO | WO 2010/121037 A1 | 10/2010 |
| WO | WO 2010/121049 A1 | 10/2010 |

OTHER PUBLICATIONS

United States Patent and Trademark Office, Final Office Action mailed Oct. 26, 2011 in U.S. Appl. No. 12/340,616, 13 pages.
United States Patent and Trademark Office, Office Action mailed Apr. 12, 2011 in U.S. Appl. No. 12/340,616, 13 pages.
United States Patent and Trademark Office, Office Action mailed Sep. 3, 2010 in U.S. Appl. No. 12/340,616, 14 pages.
WIPO, U.S. International Search Authority, International Search Report mailed Mar. 19, 2009 in International Patent Application No. PCT/US2008/087855, 2 pages.
PCT International Search Report and Written Opinion for International Patent Application No. PCT/US2008/071325, Oct. 20, 2008, 10 pages, ISA/US, Alexandria, Virginia.
United States Patent and Trademark Office, Office Action mailed Nov. 20, 2008 in U.S. Appl. No. 12/275,126, 11 pages.
Canadian Intellectual Property Office, Notice of Allowance dated Nov. 28, 2007 in Canadian Patent Application No. CA2425544, 1 page.
Canadian Intellectual Property Office, Examiner's Report dated Feb. 19, 2007 in Canadian Patent Application No. CA2425544, 2 pages.
Canadian Intellectual Property Office, Examiner's Report dated Sep. 29, 2005 in Canadian Patent Application No. CA2325544, 4 pages.
IP Australia, Examination Report dated Jun. 27, 2005 in Australian Patent Application No. AU2002214623, 3 pages.
United States Patent and Trademark Office, Notice of Allowance mailed Oct. 2, 2003 in U.S. Appl. No. 10/143,724, 11 pages.
WIPO, U.S. International Search Authority, International Search Report mailed May 28, 2002 in International Patent Application No. PCT/US2001/032588, 5 pages.
Graves, V.B. et al., "Endovascular Occlusion of the Carotid or Vertebral Artery with Temporary Proximal Flow Arrest and Microcoils: Clinical Results," *AJNR Am J Neuroradiol,* vol. 18, American Society of Neuroradiology, Aug. 1997, 6 pages.
Schmutz, F. et al., "Embolization of Cerebral Arteriovenous Malformations with Silk: Histopathologic Changes and Hemorrhagic Complications," *AJNR Am J Neuroradiol,* vol. 18, American Society of Neuroradiology, Aug. 1997, 5 pages.
Rosenthal M.D., D. et al., "Endovascular infrainguinal in situ saphenous vein bypass: A multicenter preliminary report," *J. Vasc Surg* Sep. 1992, vol. 3, No. 16, pp. 453-458, 6 pages.
Rosenthal, D. et al., "Angioscope-assisted endovascular occlusion of venous tributaries: preclinical studies," *Cardiovasc Surg* Jun. 1993, vol. 1, No. 3, pp. 225-227, 3 pages.
Vinuela M.D., F. et al., "Guglielmi detachable coil embolization of acute intracranial aneurysm: perioperative anatomical and clinical outcome in 403 patients," *J.Neurosung,* vol. 86, Mar. 1997, 8 pages.

\* cited by examiner

Direct Current (DC)
Signaling

Alternating Current (AC)
Signaling

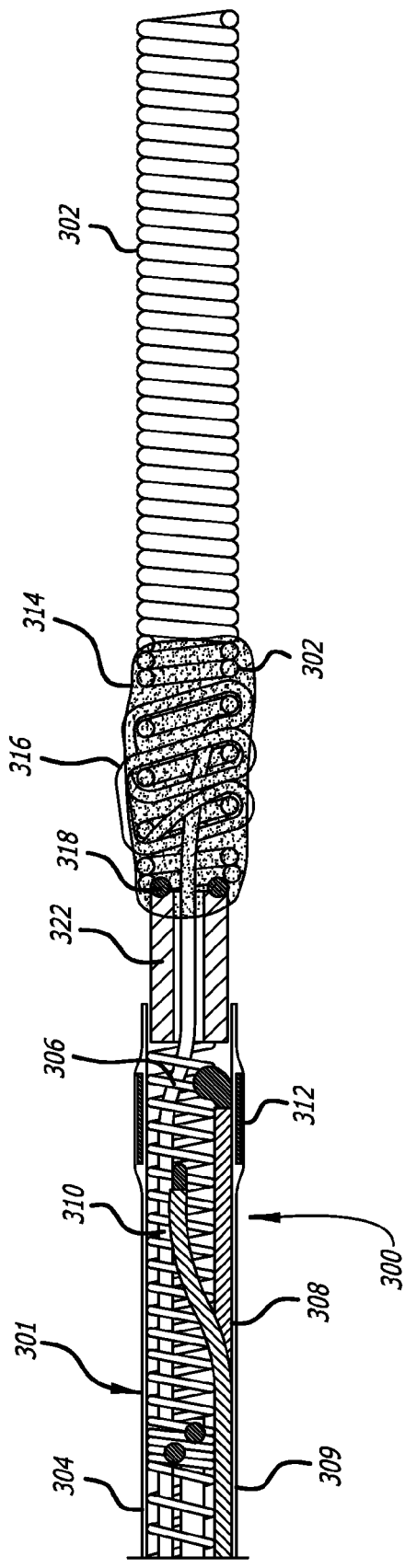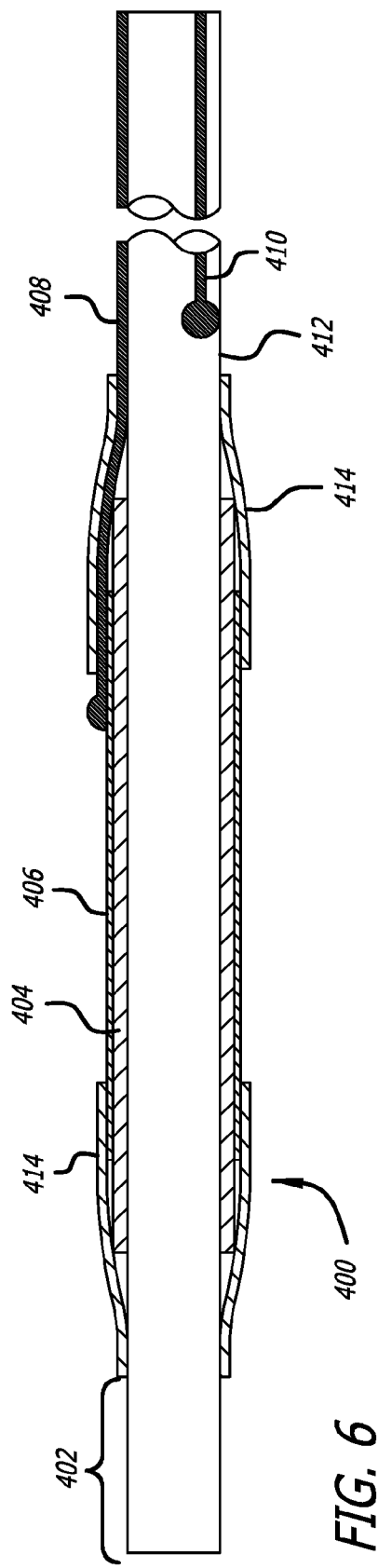

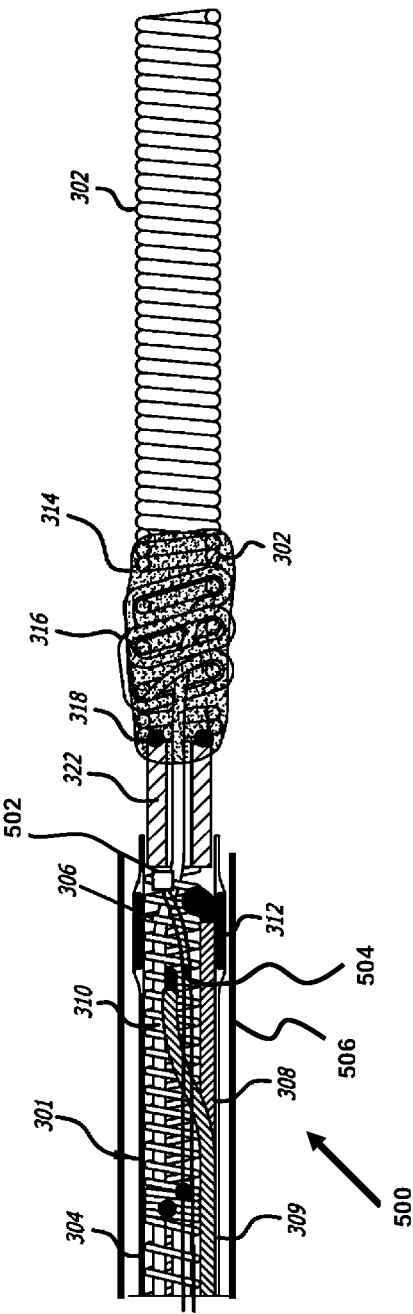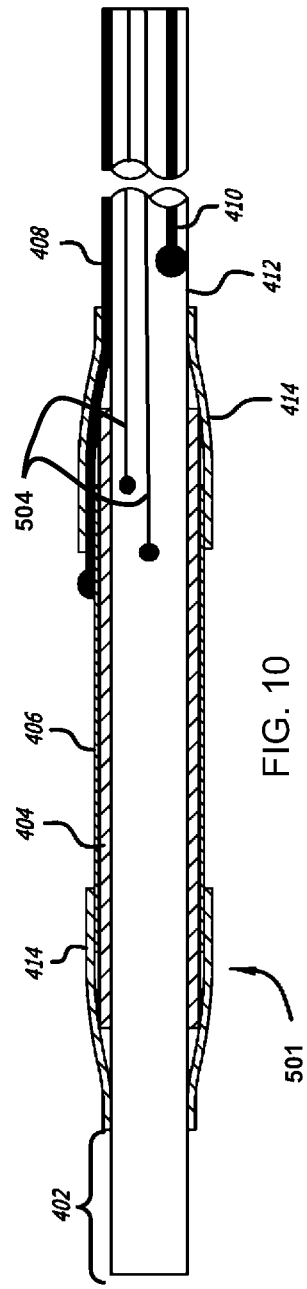

SYSTEM AND METHOD FOR LOCATING DETACHMENT ZONE OF A DETACHABLE IMPLANT

RELATED APPLICATIONS

The present application claims priority from U.S. Provisional Application Ser. No. 61/016,154, filed Dec. 21, 2007 entitled System and Method for Locating Detachment Zone of a Detachable Implant, herein incorporated by reference in its entirety. This application also incorporates by reference U.S. Provisional Application Ser. No. 60/604,671, filed Aug. 25, 2004 entitled Thermal Detachment System For Implantable Devices; U.S. Provisional Application Ser. No. 60/685,342 filed May 27, 2005 entitled Thermal Detachment System For Implantable Devices; U.S. patent application Ser. No. 11/212,830 filed Aug. 25, 2005 entitled Thermal Detachment System For Implantable Devices; U.S. Provisional Application Ser. No. 61/016,180, filed Dec. 21, 2007 entitled Method of Detecting Implant Detachment.

FIELD OF THE INVENTION

The present invention relates to systems and methods for delivering implant devices to a target site within the body of a patient. The present invention also relates to systems and methods for detecting a location of a detachment zone of a delivered implant device.

BACKGROUND OF THE INVENTION

Delivery of implantable therapeutic devices by less invasive means has been demonstrated to be desirable in numerous clinical situations. For example, vascular embolization has been used to control vascular bleeding, to occlude the blood supply to tumors, to occlude fallopian tubes, and to occlude vascular aneurysms, particularly intracranial aneurysms. In recent years, vascular embolization for the treatment of aneurysms has received much attention. As another example, the use of mesh or scaffold devices such as stents to open blocked vessels or to retain embolic coils have also received much attention.

Several different treatment modalities have been employed in the prior art for deploying implant devices. For example, numerous repositionable detachment systems for implant devices have been described in the prior art including U.S. Pat. No. 5,895,385 to Guglielmi et al. and U.S. Pat. No. 5,108,407 to Geremia et al., the contents of which are hereby incorporated by reference. Several systems, such as those disclosed in U.S. Pat. No. 6,500,149 to Gandhi et al. and U.S. Pat. No. 4,346,712 to Handa et al., the contents of which are hereby incorporated by reference, describe the use of a heater to detach and deploy the implant device.

Some percutaneously delivered detachable implant systems, such as those used to deliver occlusive coils to aneurysms, include a detachable implant that is temporarily attached to a pusher mechanism within a microcatheter. The pusher mechanism is used to advance the implant out of the distal end of the microcatheter. Once the implant has been advanced to a desired location relative to the microcatheter, referred to herein as a detachment zone, a detachment mechanism is employed to detach the implant from the pusher. It is important not to detach the implant prior to reaching the detachment zone as the implant may get hung up in the end of the catheter and subsequently get deployed at an undesirable location in the body.

Typically, in order to determine whether the implant has been advanced to the detachment zone relative to the microcatheter, radiopaque markers are used on both the microcatheter and either the pusher, the implant, or both. Thus, an operator uses the radiopaque markers to monitor the relative positions of the microcatheter and the implant as the implant is being advanced with the pusher. Monitoring the positions of the radiopaque markers requires the use of an x-ray device during the procedure. Using an x-ray imaging machine adds expense, complicates the procedure, and adds another space-consuming machine to the area surrounding the patient. Additionally, due to the coiled nature of the implant, the view of the radiopaque markers can become blocked by the coil.

SUMMARY OF THE INVENTION

The present invention is an implant delivery and detachment system used to position and deploy implantable devices such as coils, stents, filters, and the like within a body cavity including, but not limited to, blood vessels, fallopian tubes, malformations such as fistula and aneurysms, heart defects (e.g. left atrial appendages and sepal openings), and other luminal organs.

The system comprises an implant, a delivery catheter (generically referred to as the pusher or delivery pusher), a detachable joint for coupling the implant to the pusher, a heat generating apparatus (generically referred to as the heater), and a power source to apply energy to the heater.

In one aspect of the present invention, the implant is coupled to the pusher using a tether, string, thread, wire, filament, fiber, or the like. Generically this is referred to as the tether. The tether may be in the form of a monofilament, rod, ribbon, hollow tube, or the like. Many materials can be used to detachably join the implant to the pusher. One class of materials are polymers such as polyolefin, polyolefin elastomer such as those made by Dow marketed under the trade name Engage or Exxon marketed under the trade name Affinity, polyethylene, polyester (PET), polyamide (Nylon), polyurethane, polypropylene, block copolymer such as PEBAX or Hytrel, and ethylene vinyl alcohol (EVA); or rubbery materials such as silicone, latex, and Kraton. In some cases, the polymer may also be cross-linked with radiation to manipulate its tensile strength and melt temperature. Another class of materials are metals such as nickel titanium alloy (Nitinol), gold, and steel. The selection of the material depends on the capacity of the material to store potential energy, the melting or softening temperature, the power used for detachment, and the body treatment site. The tether may be joined to the implant and/or the pusher by welding, knot tying, soldering, adhesive bonding, or other means known in the art. In one embodiment where the implant is a coil, the tether may run through the inside lumen of the coil and be attached to the distal end of the coil. This design not only joins the implant to the pusher, but also imparts stretch resistance to the coil without the use of a secondary stretch resistant member. In other embodiments where the implant is a coil, stent, or filter; the tether is attached to the proximal end of the implant.

In another aspect of the present invention, the tether detachably coupling the implant to the pusher acts as a reservoir of stored (i.e. potential) energy that is released during detachment. This advantageously lowers the time and energy required to detach the implant because it allows the tether to be severed by application of heat without necessarily fully melting the material. The stored energy also may exert a force on the implant that pushes it away from the delivery catheter. This separation tends to make the system more reliable because it may prevent the tether from re-solidifying and holding the implant after detachment. Stored energy may be imparted in several ways. In one embodiment, a spring is disposed between the implant and pusher. The spring is compressed when the implant is attached to the pusher by joining one end of the tether to one of either the pusher or implant, pulling the free end of the tether until the spring is at least partially compressed, then affixing the free end of the tether to the other of the implant or the pusher. Since both ends of the tether are restrained, potential energy in the form of tension on the tether (or compression in the spring) is stored within the system. In another embodiment, one end of the tether is fixed as in the previous embodiment, and then the tether is placed in tension by pulling on the free end of the tether with a pre-determined force or displacement. When the free end of the tether is then affixed, the elongation (i.e. elastic deformation) of the tether material itself stores energy.

In another aspect of the present invention, a heater is disposed on or within the pusher, typically, but not necessarily, near the distal end of the pusher. The heater may be attached to the pusher by, for example, soldering, welding, adhesive bonding, mechanical boding, or other techniques known in the art. The heater may be in the form of a wound coil, heat pipe, hollow tube, band, hypotube, solid bar, toroid, or similar shape. The heater may be made from a variety of materials such as steel, chromium cobalt alloy, platinum, silver, gold, tantalum, tungsten, mangalin, chromium nickel alloy available from California Fine Wire Company under the trade name Stable Ohm, conductive polymer, or the like. The tether is disposed in proximity to the heater. The tether may pass through the lumen of a hollow or coil-type heater or may be wrapped around the heater. Although the tether may be disposed in direct contact with the heater, this is not necessary. For ease of assembly, the tether may be disposed be in proximity to, but not actually touching, the heater.

The delivery catheter or pusher is an elongate member with distal and proximal ends adapted to allow the implant to be maneuvered to the treatment site. The pusher comprises a core mandrel and one or more electrical leads to supply power to the heater. The pusher may taper in dimension and/or stiffness along the length, with the distal end usually being more flexible than the proximal end. In one embodiment, the pusher is adapted to be telescopically disposed within a delivery conduit such as a guide catheter or microcatheter. In another embodiment, the pusher contains an inner lumen allowing it to be maneuvered over a guide wire. In still another embodiment, the pusher can be maneuvered directly to the treatment site without a secondary device. The pusher may have a radiopaque marking system visible with fluoroscopy that allows it to be used in conjunction with radiopaque markings on the microcatheter or other adjunctive devices.

In another aspect of the present invention, the core mandrel is in the form of a solid or hollow shaft, wire, tube, hypotube, coil, ribbon, or combination thereof. The core mandrel may be made from plastic materials such as PEEK, acrylic, polyamide, polyimide, Teflon, acrylic, polyester, block copolymer such as PEBAX, or the like. The plastic member(s) may be selectively stiffened along the length with reinforcing fibers or wires made from metal, glass, carbon fiber, braid, coils, or the like. Alternatively, or in combination with plastic components, metallic materials such as stainless steel, tungsten, chromium cobalt alloy, silver, copper, gold, platinum, titanium, nickel titanium alloy (Nitinol), and the like may be used to form the core mandrel. Alternatively, or in combination with plastic and/or metallic components, ceramic components such as glass, optical fiber, zirconium, or the like may be used to form the core mandrel. The core mandrel may also be a composite of materials. In one embodiment, the core mandrel comprises an inner core of radiopaque material such as platinum or tantalum and an outer covering of kink-resistant material such as steel or chromium cobalt. By selectively varying the thickness of the inner core, radiopaque identifiers can be provided on the pusher without using secondary markers. In another embodiment, a core material, for example stainless steel, with desirable material properties such as kink resistance and/or compressive strength is selectively covered (by, for example, plating, drawing, or similar methods known in the art) with a low electrical resistance material such as copper, aluminum, gold, or silver to enhance its electrical conductivity, thus allowing the core mandrel to be used as an electrical conductor. In another embodiment, a core material, for example, glass or optical fiber, with desirable properties such as compatibility with Magnetic Resonance Imaging (MRI), is covered with a plastic material such as PEBAX or polyimide to prevent the glass from fracturing or kinking.

In another aspect of the present invention, the heater is attached to the pusher, and then one or more electrical conductors are attached to the heater. In one embodiment a two of conductive wires run substantially the length of the pusher and are coupled to the heater near the distal end of the pusher and to electrical connectors near the proximal end of the pusher. In another embodiment, one conductive wire runs the substantially the length of the pusher and the core mandrel itself is made from a conductive material or coated with a conductive material to act as a second electrical lead. The wire and the mandrel are coupled to the heater near the distal end and to one or more connectors near the proximal end of the pusher. In another embodiment, a bipolar conductor is coupled to the heater and is used in conjunction with radiofrequency (RF) energy to power the heater. In any of the embodiments, the conductor(s) may run in parallel to the core mandrel or may pass through the inner lumen of a substantially hollow core mandrel (for example, a hypotube).

In another aspect of the present invention, an electrical and/or thermally insulating cover or sleeve may be placed over the heater. The sleeve may be made from insulating materials such as polyester (PET), Teflon, block copolymer, silicone, polyimide, polyamide, and the like.

In another aspect of the present invention, electrical connector(s) are disposed near the proximal end of the pusher so that the heater can be electrically connected to a power source through the conductors. In one embodiment, the connectors are in the form of a plug with one or more male or female pins. In another embodiment, the connector(s) are tubes, pins, or foil that can be connected with clip-type connectors. In another embodiment, the connector(s) are tubes, pins, or foil that are adapted to mate with an external power supply.

In another aspect of the present invention, the pusher connects to an external power source so that the heater is electrically coupled to the power source. The power source may be from battery(s) or connected to the electrical grid by a wall outlet. The power source supplies current in the form of direct current (DC), alternating current (AC), modulated direct current, or radiofrequency (RF) at either high or low frequency. The power source may be a control box that operates outside of the sterile field or may be a hand-held device adapted to operate within a sterile field. The power source may be disposable, rechargeable, or may be reusable with disposable or rechargeable battery(s).

In another aspect of the present invention, the power source may comprise an electronic circuit that assists the user with detachment. In one embodiment, the circuit detects detachment of the implant and provides a signal to the user when detachment has occurred. In another embodiment, the circuit comprises a timer that provides a signal to the user when a pre-set length of time has elapsed. In another embodiment, the circuit monitors the number of detachments and provides a signal or performs an operation such as locking the system off when a pre-set number of detachments have been performed. In another embodiment, the circuit comprises a feedback loop that monitors the number of detachment attempts and increases the current, voltage, and/or detachment time in order to increase the likelihood of a successful detachment.

In another aspect of the present invention, the construction of the system allows for extremely short detachment time. In one embodiment the detachment time is less than 1 second.

In another aspect of the present invention, the construction of the system minimizes the surface temperature of the device during detachment. In one embodiment, the surface temperature at the heater during detachment is under 50° C. In another embodiment, the surface temperature at the heater during detachment is under 42° C.

The present invention is also a method and system for detecting the location of the detachment zone of a detachable coil as it exits the distal tip of the microcatheter without using radiopaque markers. Various sensing techniques are used to detect a change in various corresponding parameters due to the environmental difference between the inside of the microcatheter and exposure to a target site in the body.

In another aspect of the present invention a temperature sensor is utilized to detect a change in temperature as the sensor exits the microcatheter. The change in temperatures indicates that the detachable implant is in a desired detachment zone.

In another aspect of the present invention a pressure sensor is utilized to detect a change in pressure as the sensor exits the microcatheter. The change in pressure indicates that the detachable implant is in a desired detachment zone.

In another aspect of the present invention an ultrasound sensor is utilized to detect a change in environmental space as the sensor exits the microcatheter. When inside the microcatheter, the ultrasonic sensor detects the distance to the inner walls of the microcatheter. When outside the microcatheter, the ultrasonic sensor detects the increased distance to the inner walls of the vascular lumen or aneurysm. Hence, the change in distance indicates that the detachable implant is in a desired detachment zone.

Yet another aspect of the present invention the detachable coil is utilized as a detection mechanism. During navigation to the target site, the coil is contained, in a straight configuration, within the microcatheter. As the coil is pushed out of the microcatheter, it regains a curved configuration. If an electrical current is passed through the coil, the resistance to current flow through the coil changes as it curves. This change in resistance is used as a detection mechanism.

These and other aspects and features of the present invention will be appreciated upon consideration of the following drawings and detailed descriptions.

BRIEF DESCRIPTION OF THE DRAWINGS

FIG. 4 illustrates a cross-sectional side view of a third embodiment of a detachment system according to the present invention;

FIG. 6 illustrates a cross-sectional side view of an electrical connector of a detachment system according to the present invention;

FIG. 9 illustrates a partially exploded perspective view of a delivery system according to the present invention;

FIG. 10 illustrates a cross-sectional side view of an electrical connector of a detachment system according to the present invention.

DETAILED DESCRIPTION OF THE INVENTION

Figure 1:
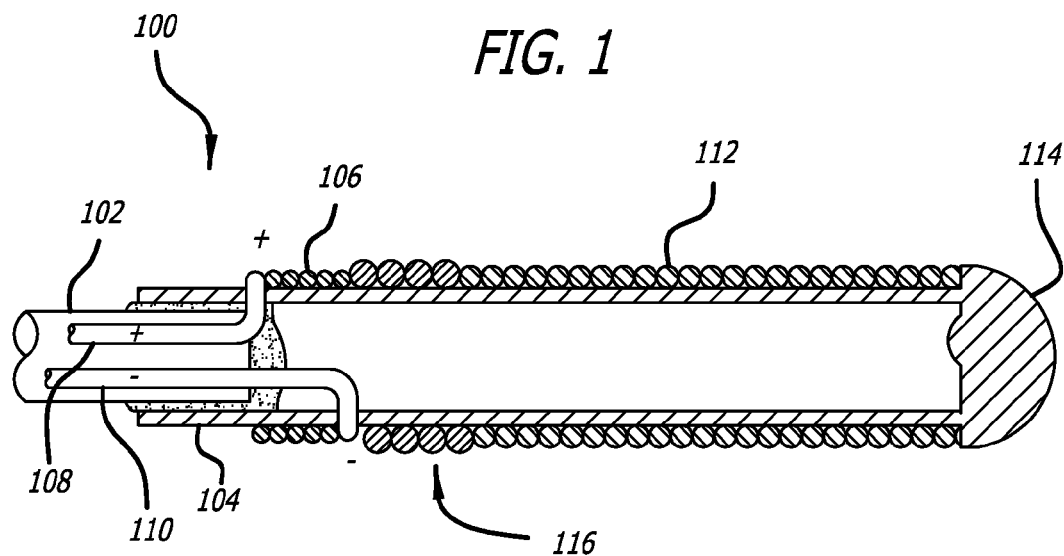
FIG. 1 illustrates a cross-sectional side view of a first embodiment of a detachment system according to the present invention.

Turning to FIG. 1, a detachment system 100 of the present invention, and specifically the distal portion of the detachment system 100, is illustrated. The detachment system 100 includes a pusher 102 that is preferably flexible. The pusher 102 is configured for use in advancing an implant device 112 into and within the body of a patient and, specifically, into a target cavity site for implantation and delivery of the implant device 112. Potential target cavity sites include but are not limited to blood vessels and vascular sites, such as, e.g., aneurysms and fistula, heart openings and defects, such as, e.g., the left atrial appendage, and other luminal organs, such as, e.g., fallopian tubes.

A stretch-resistant tether 104 detachably couples the implant 112 to the pusher 102. In this example, the tether 104 is a plastic tube that is bonded to the pusher 102. A substantially solid cylinder could also be a design choice for the tether 104. The stretch resistant tether 104 extends at least partially through the interior lumen of an implant device 112.

Near the distal end of the pusher 102, a heater 106 is disposed in proximity to the stretch resistant tether 104. The heater 106 may be wrapped around the stretch resistant tether 104 such that the heater 106 is exposed to or otherwise in direct contact with the blood or the environment, or alternatively may be insulated by a sleeve, jacket, epoxy, adhesive, or the like. The pusher 102 comprises a pair of electrical wires, positive electrical wire 108 and negative electrical wire 110. The wires 108 and 110 are coupled to the heater 106 by any suitable means, such as, e.g., by welding or soldering.

The electrical wires 108, 110 are capable of being coupled to a source of electrical power (not shown). As illustrated the negative electrical wire 110 is coupled to the distal end of the heater 106 and the positive electrical wire 108 is coupled to the proximal end of the heater 106. In another embodiment, this configuration may be reversed, i.e., the negative electrical wire 110 is coupled to the proximal end of the heater 106 while the positive electrical wire 108 is coupled to the distal end of the heater 106.

Energy is applied to the heater 106 from the electrical wires 108, 110 in order to sever the portion of the tether 104 in the proximity of the heater 106. It is not necessary for the heater 106 to be in direct contact with the tether 104. The heater 106 merely should be in sufficient proximity to the tether 104 so that heat generated by the heater 106 causes the tether 104 to sever. As a result of activating the heater 106, the section of the stretch resistant tether 104 that is approximately distal from the heater 106 and within the lumen of an implant device 112 is released from the pusher 102 along with the implant device 112.

As illustrated, the implant device 112 is an embolic coil. An embolic coil suitable for use as the implant device 112 may comprise a suitable length of wire formed into a helical microcoil. The coil may be formed from a biocompatible material including platinum, rhodium, palladium, rhenium, tungsten, gold, silver, tantalum, and various alloys of these metals, as well as various surgical grade stainless steels. Specific materials include the platinum/tungsten alloy known as Platinum 479 (92% Pt, 8% W, available from Sigmund Cohn, of Mount Vernon, N.Y.) and nickel/titanium alloys (such as the nickel/titanium alloy known as Nitinol).

Another material that may be advantageous for forming the coil is a bimetallic wire comprising a highly elastic metal with a highly radiopaque metal. Such a bimetallic wire would also be resistant to permanent deformation. An example of such a bimetallic wire is a product comprising a Nitinol outer layer and an inner core of pure reference grade platinum, available from Sigmund Cohn, of Mount Vernon, N.Y., and Anomet Products, of Shrewsbury, Mass.

Commonly-assigned U.S. Pat. No. 6,605,101 provides a further description of embolic coils suitable for use as the implant device 112, including coils with primary and secondary configurations wherein the secondary configuration minimizes the degree of undesired compaction of the coil after deployment. The disclosure of U.S. Pat. No. 6,605,101 is fully incorporated herein by reference. Furthermore, the implant device 112 may optionally be coated or covered with a hydrogel or a bioactive coating known in the art.

The coil-type implant device 112 resists unwinding because the stretch resistant tether 104 that extends through the lumen of the implant device 112 requires substantially more force to plastically deform than the implant device 112 itself. The stretch resistant tether 104 therefore assists in preventing the implant device 112 from unwinding in situations in which the implant device 112 would otherwise unwind.

During assembly, potential energy may be stored within the device to facilitate detachment. In one embodiment, an optional spring 116 is placed between the heater 106 and the implant device 112. The spring is compressed during assembly and the distal end of the tether 104 may be tied or coupled to the distal end of the implant device 112, or may be melted or otherwise formed into an atraumatic distal end 114.

In one embodiment, the stretch resistant tether 104 is made from a material such as a polyolefin elastomer, polyethylene, or polypropylene. One end of the tether 104 is attached to the pusher 102 and the free end of the tether 104 is pulled through the implant 112 with the proximal end of the implant 112 flush to either the heater 106 (if no spring 116 is present) or to the compressed spring 116. A pre-set force or displacement is used to pre-tension the tether 104, thus storing energy in an axial orientation (i.e. co-linear or parallel to the long axis of the pusher 102) within the tether 104. The force or displacement depends on the tether material properties, the length of the tether 104 (which itself depends on the tether's attachment point on the pusher and the length of the implant). Generally, the force is below the elastic limit of the tether material, but sufficient to cause the tether to sever quickly when heat is applied. In one preferred embodiment wherein the implant to be deployed is a cerebral coil, the tether has a diameter within the range of approximately 0.001 to 0.007 inches. Of course the size of the tether can be changed to accommodate different types and sizes of other implants as necessary.

Figure 2:
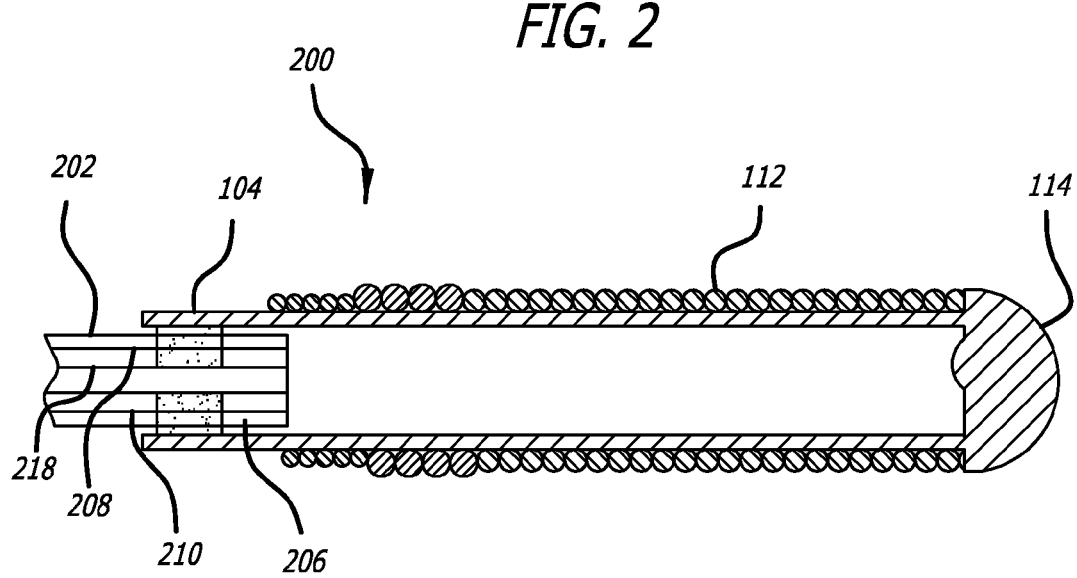
FIG. 2 illustrates a cross-sectional side view of a second embodiment of a detachment system according to the present invention.

Turning to FIG. 2, another embodiment of a detachment system of the present invention, detachment system 200, is illustrated. Detachment system 200 shares several common elements with detachment system 100. For example, the same devices usable as the implant device 112 with detachment system 100 are also usable as the implant device 112 with detachment system 200. These include, e.g., various embolic microcoils and coils. The implant device 112 has been previously described with respect to detachment system 100. As with the implant device 112, the same identification numbers are used to identify other elements/components of detachment system 100 that may correspond to elements/components of detachment system 200. Reference is made to the description of these elements in the description of detachment system 100 as that description also applies to these common elements in detachment system 200.

With detachment system 200, an interior heating element 206 is used to separate a section of a stretch resistant tube 104 and an associated implant device 112 from the detachment system 200. Detachment system 200 includes a delivery pusher 202 that incorporates a core mandrel 218. The detachment system 200 further includes a positive electrical wire 208 and a negative electrical wire 210 that extend through the lumen of the delivery pusher 202.

To form the internal heating element 206, the positive electrical wire 208 and the negative electrical wire 210 may be coupled to the core mandrel 218 of the delivery pusher 202. Preferably, the electrical wires 208, 210 are coupled to a distal portion of the core mandrel 218.

In one embodiment, the positive electrical wire 208 is coupled to a first distal location on the core wire 218, and the negative electrical wire 210 is coupled to a second distal location on the core wire 218, with the second distal location being proximal to the first distal location. In another embodiment, the configuration is reversed, i.e., the positive electrical wire 208 is coupled to the second distal location and the negative electrical wire 210 is coupled to the first distal location on the core wire 218. When the positive electrical wire 208 and the negative electrical wire 210 are coupled to the distal portion of the core mandrel 218, the distal portion of the core mandrel 218 along with the electrical wires 208, 210 forms a circuit that is the interior heating element 206.

The heater 206 increases in temperature when a current is applied from a power source (not shown) that is coupled to the positive electrical wire 208 and the negative electrical wire 210. If a greater increase in temperature/higher degree of heat is required or desired, a relatively high resistance material such as platinum or tungsten may be coupled to the distal end of the core mandrel 218 to increase the resistance of the core mandrel 218. As a result, higher temperature increases are produced when a current is applied to the heater 206 than would be produced with a lower resistance material. The additional relatively high resistance material coupled to the distal end of the core mandrel 218 may take any suitable form, such as, e.g., a solid wire, a coil, or any other shape or material as described above.

Because the heater 206 is located within the lumen of the tube-shaped tether 104, the heater 206 is insulated from the body of the patient. As a result, the possibility of inadvertent damage to the surrounding body tissue due to the heating of the heater 206 may be reduced.

When a current is applied to the heater 206 formed by the core mandrel 218, the positive electrical wire 208, and the negative electrical wire 210, the heater 206 increases in temperature. As a result, the portion of the stretch resistant tether 104 in proximity to the heater 206 severs and is detached, along with the implant device 112 that is coupled to the tether 104, from the detachment system 200.

In one embodiment of the detachment system 200, the proximal end of the stretch resistant tether 104 (or the distal end of a larger tube (not shown) coupled to the proximal end of the stretch resistant tether 104) may be flared in order to address size constraints and facilitate the assembly of the detachment system 200.

In a similar manner as with detachment system 100, energy may be stored within the system with, for example, an optional compressive spring 116 or by pre-tensioning the tether 104 during assembly as previously described. When present, the release of potential energy stored in the system operates to apply additional pressure to separate the implant device 112, and the portion of the stretch resistant tether 104 to which the implant device 112 is coupled, away from the heater 206 when the implant device 112 is deployed. This advantageously lowers the required detachment time and temperature by causing the tether 104 to sever and break.

As with detachment system 100, the distal end of the stretch resistant tether 104 of detachment system 200 may be tied or coupled to the distal end of the implant device 112, or may be melted or otherwise formed into an atraumatic distal end 114.

FIG. 4 illustrates another preferred embodiment of a detachment system 300. In many respects, the detachment system 300 is similar to the detachment system 200 shown in FIG. 2 and detachment system 100 shown in FIG. 1. For example, the detachment system 300 includes a delivery pusher 301 containing a heater 306 that detaches an implant device 302. Detachment system 300 also utilizes a tether 310 to couple the implant device 302 to the delivery pusher 301.

In the cross-sectional view of FIG. 4, a distal end of the delivery pusher 301 is seen to have a coil-shaped heater 306 that is electrically coupled to electrical wires 308 and 309. These wires 308, 309 are disposed within the delivery pusher 301, exiting at a proximal end of the delivery pusher 301 and coupling to a power supply (not shown). The tether 310 is disposed in proximity to the heater 306, having a proximal end fixed within the delivery pusher 301 and a distal end coupled to the implant device 302. As current is applied through wires 308 and 309, the heater 306 increases in temperature until the tether 310 breaks, releasing the implant device 302.

To reduce the transfer of heat from the heater 306 to the surrounding tissue of the patient and to provide electrical insulation, an insulating cover 304 is included around at least the distal end of the outer surface of the delivery pusher 301. As the thickness of the cover 304 increases, the thermal insulating properties also increase. However, increased thickness also brings increased stiffness and a greater diameter to the delivery pusher 301 that could increase the difficulty of performing a delivery procedure. Thus, the cover 304 is designed with a thickness that provides sufficient thermal insulating properties without overly increasing its stiffness.

To enhance attachment of the tether 310 to the implant device 302, the implant device 302 may include a collar member 322 welded to the implant device 302 at weld 318 and sized to fit within the outer reinforced circumference 312 of the delivery pusher 301. The tether 310 ties around the proximal end of the implant device 302 to form knot 316. Further reinforcement is provided by an adhesive 314 that is disposed around the knot 316 to prevent untying or otherwise unwanted decoupling.

In a similar manner as with detachment systems 100 and 200, energy may be stored within the system with, for example, an optional compressive spring (similar to compressive spring 116 in FIG. 1 but not shown in FIG. 4) or by axially pre-tensioning the tether 104 during assembly. In this embodiment, one end of the tether 310 is attached near the proximal end of the implant device 302 as previously described. The free end of the tether 310 is threaded through a distal portion of the delivery pusher 301 until it reaches an exit point (not shown) of the delivery pusher 301. Tension is applied to the tether 310 in order to store energy in the form of elastic deformation within the tether material by, for example, placing a pre-determined force on the free end of the tether 310 or moving the taunt tether 310 a pre-determined displacement. The free end of the tether 310 is then joined to the delivery pusher 301 by, for example, tying a knot, applying adhesive, or similar methods known in the art.

When present, the release of potential energy stored in the system operates to apply additional pressure to separate the implant device 302, and the portion of the tether 310 to which the implant device 302 is coupled, away from the heater 306 when the implant device 302 is deployed. This advantageously lowers the required detachment time and temperature by causing the tether 310 to sever and break.

The present invention also provides for methods of using detachment systems such as detachment systems 100, 200, or 300. The following example relates to the use of detachment system 100, 200, or 300 for occluding cerebral aneurysms. It will, however, be appreciated that modifying the dimensions of the detachment system 100, 200, or 300 and the component parts thereof and/or modifying the implant device 112, 302 configuration will allow the detachment system 100, 200, or 300 to be used to treat a variety of other malformations within a body.

With this particular example, the delivery pusher 102, 202, or 301 of the detachment system 100, 200, or 300 may be approximately 0.010 inches to 0.030 inches in diameter. The tether 104, 310 that is coupled near the distal end of the delivery pusher 102, 202, or 301 and is coupled the implant device 112, 302 may be 0.0002 inches to 0.020 inches in diameter. The implant device 112, 302; which may be a coil, may be approximately 0.005 inches to 0.020 inches in diameter and may be wound from 0.0005 inch to 0.005 inch wire.

If potential energy is stored within the detachment system 100, 200, or 300, the force used to separate the implant 112, 302 from the pusher typically ranges up to 250 grams force.

The delivery pusher 102, 202, or 301 may comprise a core mandrel 218 and at least one electrically conductive wire 108, 110, 208, 210, 308, or 309. The core mandrel 218 may be used as an electrical conductor, or a pair of conductive wires may be used, or a bipolar wire may be used as previously described.

Figure 8:
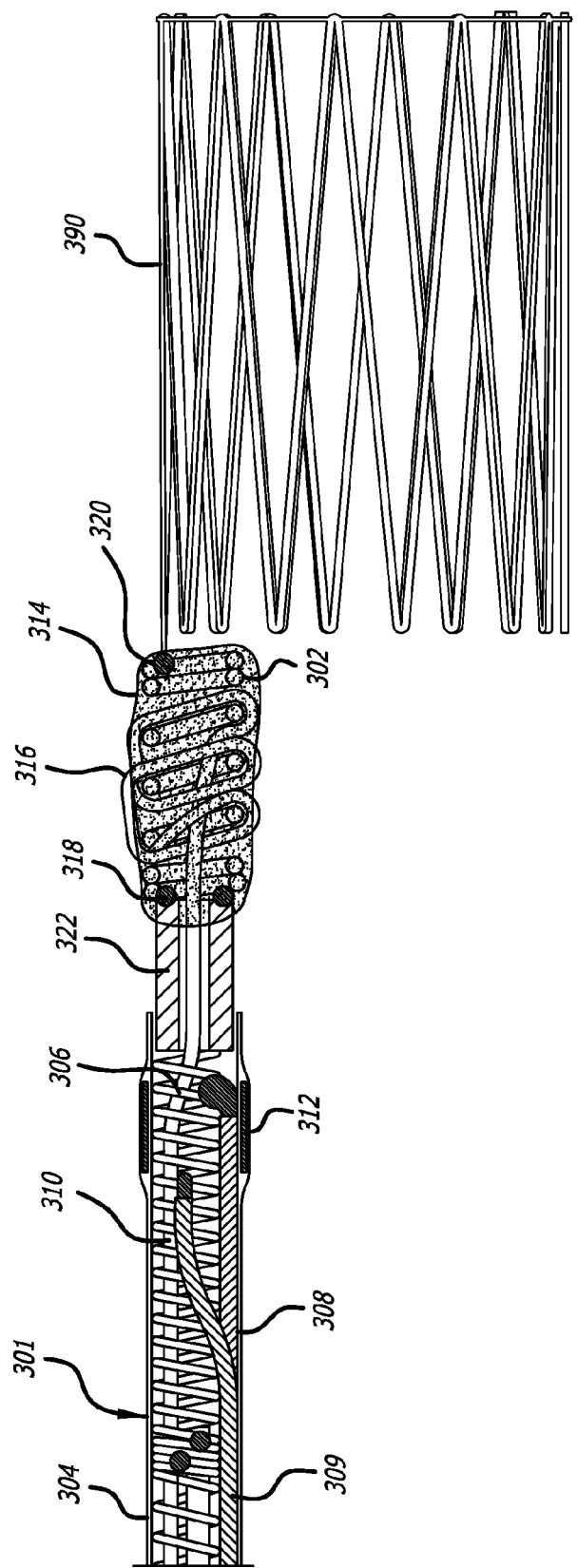
FIG. 8 illustrates a cross-sectional side view of a detachment system including a stent according to the present invention.

Although the detachment systems 100, 200, and 300 have been illustrated as delivering a coil, other implant devices are contemplated in the present invention. For example, FIG. 8 illustrates the detachment system 300 as previously described in FIG. 4 having an implant that is a stent 390. This stent 390 could similarly be detached by a similar method as previously described in regards to the detachment systems 100, 200, and 300. In a further example, the detachment systems 100, 200, or 300 may be used to deliver a filter, mesh, scaffolding or other medical implant suitable for delivery within a patient.

Figure 7:
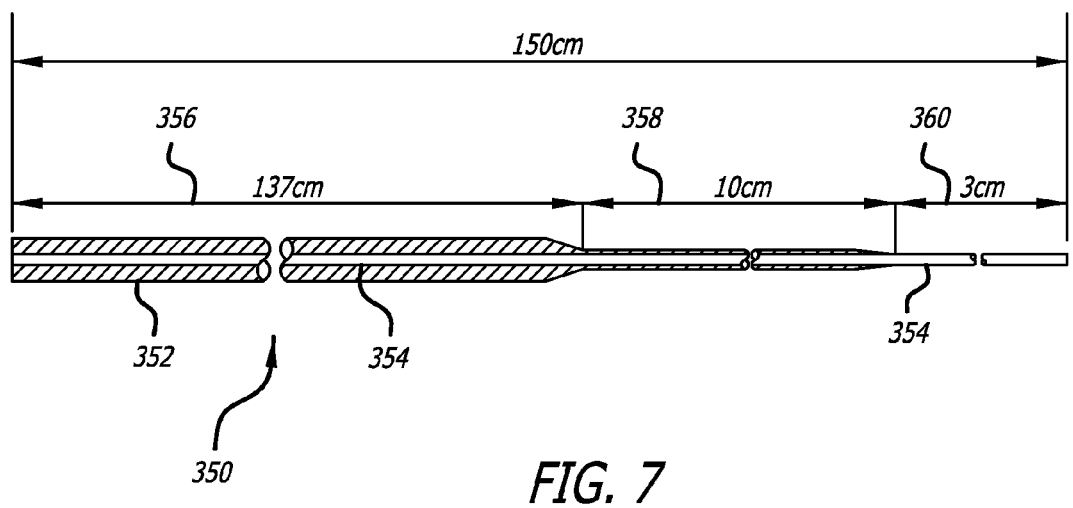
FIG. 7 illustrates a cross-sectional side view of radiopaque layers of a detachment system according to the present invention.

FIG. 7 presents an embodiment of a delivery pusher 350, which could be used in any of the embodiments as delivery pusher 102, 202, or 301, which includes radiopaque materials to communicate the position of the delivery pusher 350 to the user. Specifically, the radiopaque marker material is integrated into the delivery pusher 350 and varied in thickness at a desired location, facilitating easier and more precise manufacturing of the final delivery pusher 350.

Prior delivery pusher designs, such as those seen in U.S. Pat. No. 5,895,385 to Guglielmi, herein incorporated by reference, rely on high-density material such as gold, tantalum, tungsten, or platinum in the form of an annular band or coil. The radiopaque marker is then bonded to other, less dense materials, such as stainless steel, to differentiate the radiopaque section. Since the radiopaque marker is a separate element placed at a specified distance (often about 3 cm) from the tip of the delivery pusher, the placement must be exact or the distal tip of the delivery pusher 350 can result in damage to the aneurysm or other complications. For example, the delivery pusher 350 may be overextended from the microcatheter to puncture an aneurysm. Additionally, the manufacturing process to make a prior delivery pusher can be difficult and expensive, especially when bonding dissimilar materials.

The radiopaque system of the present invention overcomes these disadvantages by integrating a first radiopaque material into most of the delivery pusher 350 while varying the thickness of a second radiopaque material, thus eliminating the need to bond multiple sections together. As seen in FIG. 7, the delivery pusher 350 comprises a core mandrel 354 (i.e. the first radiopaque material), preferably made from radiopaque material such as tungsten, tantalum, platinum, or gold (as opposed to the mostly radiolucent materials of the prior art designs such as steel, Nitinol, and Elgiloy).

The delivery pusher 350 also includes a second, outer layer 352, having a different radiopaque level. Preferably, outer layer 352 is composed of a material having a lower radiopaque value than the core mandrel 354, such as Elgiloy, Nitinol, or stainless steel (commercially available from Fort Wayne Metals under the trade name DFT). In this respect, both the core mandrel 354 and the outer layer 352 are visible and distinguishable from each other under fluoroscopy. The outer layer 352 varies in thickness along the length of the delivery pusher 350 to provide increased flexibility and differentiation in radio-density. Thus the thicker regions of the outer layer 352 are more apparent to the user than the thinner regions under fluoroscopy.

The transitions in thickness of the outer layer 352 can be precisely created at desired locations with automated processes such as grinding, drawing, or forging. Such automated processes eliminate the need for hand measuring and placement of markers and further eliminates the need to bond a separate marker element to other radiolucent sections, thus reducing the manufacturing cost and complexity of the system.

In the present embodiment, the delivery pusher 350 includes three main indicator regions of the outer layer 352. A proximal region 356 is the longest of the three at 137 cm, while a middle region 358 is 10 cm and a distal region 360 is 3 cm. The length of each region can be determined based on the use of the delivery pusher 350. For example, the 3 cm distal region 360 may be used during a coil implant procedure, as known in the art, allowing the user to align the proximal edge of the distal region 360 with a radiopaque marker on the microcatheter within which the delivery pusher 350 is positioned. The diameter of each of the regions depends on the application and size of the implant. For a typical cerebral aneurysm application for example, the proximal region 356 may typically measure 0.005-0.015 inches, the middle region 358 may typically measure 0.001-0.008 inches, while the distal region 360 may typically measure 0.0005-0.010 inches. The core mandrel 354 will typically comprise between about 10-80% of the total diameter of the delivery pusher 350 at any point.

Alternately, the delivery pusher 350 may include any number of different regions greater than or less than the three shown in FIG. 7. Additionally, the radiopaque material of the core mandrel 354 may only extend partially through the delivery pusher 350. For example, the radiopaque material could extend from the proximal end of the core mandrel 354 to three centimeters from the distal end of the delivery pusher 350, providing yet another predetermined position marker visible under fluoroscopy.

In this respect, the regions 356, 358, and 360 of delivery pusher 350 provide a more precise radiopaque marking system that is easily manufactured, yet is readily apparent under fluoroscopy. Further, the increased precision of the markers may decrease complications relating to improper positioning of the delivery pusher during a procedure.

In operation, the microcatheter is positioned within a patient so that a distal end of the microcatheter is near a target area or lumen. The delivery pusher 350 is inserted into the proximal end of the microcatheter and the core mandrel 354 and outer layer 352 are viewed under fluoroscopy. The user aligns a radiopaque marker on the microcatheter with the beginning of the distal region 360, which communicates the location of the implant 112, 302 relative to the tip of the microcatheter.

In some situations, for example, small aneurysms where there may be an elevated risk of vessel damage from the stiffness of the delivery pusher 350, the user may position the proximal end of the implant slightly within the distal end of the microcatheter during detachment. The user then may push the proximal end of the implant 112, 302 out of the microcatheter with the next coil, an adjunctive device such as guidewire, or the delivery pusher 102, 202, 301, or 350. In another embodiment, the user may use the radiopaque marking system to locate the distal end of the delivery pusher outside the distal end of the microcatheter.

Once the implant device 112, 302 of the detachment system 100, 200, or 300 is placed in or around the target site, the operator may repeatedly reposition the implant device 112, 302 as necessary or desired.

When detachment of the implant device 112, 302 at the target site is desired, the operator applies energy to the heater 106, 206, or 306 by way of the electrical wires 108, 110, 208, 210, 308, or 309. The electrical power source for the energy may be any suitable source, such as, e.g., a wall outlet, a capacitor, a battery, and the like. For one aspect of this method, electricity with a potential of approximately 1 volt to 100 volts is used to generate a current of 1 milliamp to 5000 milliamps, depending on the resistance of the detachment system 100, 200, or 300.

One embodiment of a connector system 400 that can be used to electrically couple the detachment system 100, 200, or 300 to the power source is shown in FIG. 6. The connector system 400 includes an electrically conductive core mandrel 412 having a proximal end surrounded by an insulating layer 404. Preferably the insulating layer 404 is an insulating sleeve such as a plastic shrink tube of polyolefin, PET, Nylon, PEEK, Teflon, or polyimide. The insulating layer 404 may also be a coating such as polyurethane, silicone, Teflon, paralyene. An electrically conductive band 406 is disposed on top of the insulating layer 404 and secured in place by molding bands 414, adhesive, or epoxy. Thus, the core mandrel 412 and the conductive band 406 are electrically insulated from each other. The conductive band 406 is preferably composed of any electrically conductive material, such as silver, gold, platinum, steel, copper, conductive polymer, conductive adhesive, or similar materials, and can be a band, coil, or foil. Gold is especially preferred as the conductive material of the conductive band 406 because of the ability of gold to be drawn into a thin wall and its ready availability. The core mandrel 412 has been previously described and may be plated with, for example, gold, silver, copper, or aluminum to enhance its electrical conductivity.

The connector system 400 also includes two electrical wires 408 and 410 which connect to the conductive band 406 and core member 412, respectively, and to a heating element at the distal end of a delivery system such as those described in FIGS. 1, 2, and 4 (not shown in FIG. 6). These wires 408 and 410 are preferably connected by soldering, brazing, welding, laser bonding, or conductive adhesive, or similar techniques.

Once the user is ready to release the implant 112, 302 within the patient, a first electrical clip or connector from a power source is connected to a non-insulated section 402 of the core mandrel 412 and a second electrical clip or connector from the power source is connected to the conductive band 406. Electrical power is applied to the first and second electrical clips, forming an electrical circuit within the detachment system 100, 200, or 300, causing the heater 106, 206, or 306 to increase in temperature and sever the tether 104, 310.

Once the detachment system 100, 200, or 300 is connected to the power source the user may apply a voltage or current as previously described. This causes the heater 106, 206, or 306 to increase in temperature. When heated, the pre-tensioned tether 104, 310 will tend to recover to its unstressed (shorter) length due to heat-induced creep. In this respect, when the tether 104, 310 is heated by the heater 106, 206, or 306; its overall size shrinks. However, since each end of the tether 104, 310 is fixed in place as previously described, the tether 104, 310 is unable to shorten in length, ultimately breaking to release the implant device 112, 302.

Because there is tension already within the system in the form of a spring 116 or deformation of the tether material 104, 310; the amount of shrinkage required to break the tether 104, 310 is less than that of a system without a pre-tensioned tether. Thus, the temperature and time required to free the implant device 112, 302 is lower.

Figure 5:
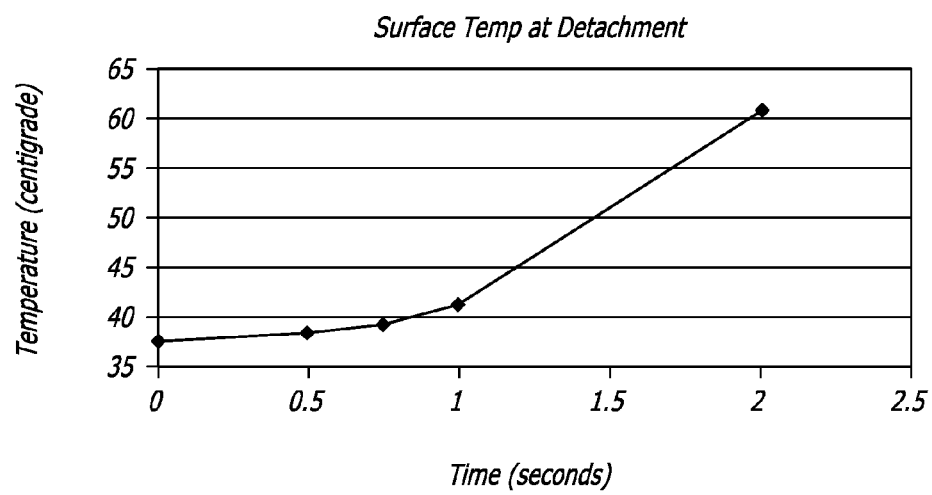
FIG. 5 illustrates example temperature data of the surface of a detachment system as a function of time according to the present invention.

FIG. 5 is a graph showing the relationship between the temperature at the surface of PET cover 304 of the detachment system 300 and the time duration in which the heater coil 306 is activated. As can be seen, the surface temperature of the detachment system 300 during detachment does not vary linearly with time. Specifically, it takes just under 1 second for the heat generated by the heating coil 306 to penetrate the insulating cover 304. After 1 second, the surface temperature of the insulating cover 304 dramatically increases. Although different outer insulating material may slightly increase or decrease this 1-second surface temperature window, the necessarily small diameter of the detachment system 100, 200, or 300 prevents providing a thick insulating layer that may more significantly delay a surface temperature increase.

It should be understood that the embodiments of the detachment system 100, 200, or 300 include a variety of possible constructions. For example, the insulating cover 304 may be composed of Teflon, PET, polyamide, polyimide, silicone, polyurethane, PEEK, or materials with similar characteristics. In the embodiments 100, 200, or 300 the typical thickness of the insulating cover is 0.0001-0.040 inches. This thickness will tend to increase when the device is adapted for use in, for example, proximal malformations, and decrease when the device is adapted for use in more distal, tortuous locations such as, for example, cerebral aneurysms.

In order to minimize the damage and possible complications caused by such a surface temperature increase, the present invention detaches the implant device 112, 302 before the surface temperature begins to significantly increase. Preferably, the implant device 112, 302 is detached in less than a second, and more preferably, in less than 0.75 seconds. This prevents the surface temperature from exceeding 50° C. (122° F.), and more preferably, from exceeding 42° C. (107° F.).

Once the user attempts to detach the implant device 112, 302, it is often necessary to confirm that the detachment has been successful. The circuitry integrated into the power source may be used to determine whether or not the detachment has been successful. In one embodiment of the present invention an initial signaling current is provided prior to applying a detachment current (i.e. current to activate the heater 106, 206, or 306 to detach an implant 112, 302). The signaling current is used to determine the inductance in the system before the user attempts to detach the implant and therefore has a lower value than the detachment current, so as not to cause premature detachment. After an attempted detachment, a similar signaling current is used to determine a second inductance value that is compared to the initial inductance value. A substantial difference between the initial inductance and the second inductance value indicates that the implant 112, 302 has successfully been detached, while the absence of such a difference indicates unsuccessful detachment. In this respect, the user can easily determine if the implant 112, 302 has been detached, even for delivery systems that utilize nonconductive temperature sensitive polymers to attach an implant, such as those seen in FIGS. 1, 2, and 4.

In the following description and examples, the terms "current" and "electrical current" are used in the most general sense and are understood to encompass alternating current (AC), direct current (DC), and radiofreqeuncy current (RF) unless otherwise noted. The term "changing" is defined as any change in current with a frequency above zero, including both high frequency and low frequency. When a value is measured, calculated and/or saved, it is understood that this may be done either manually or by any known electronic method including, but not limited to, an electronic circuit, semiconductor, EPROM, computer chip, computer memory such as RAM, ROM, or flash; and the like. Finally, wire windings and toroid shapes carry a broad meaning and include a variety of geometries such as circular, elliptical, spherical, quadrilateral, triangular, and trapezoidal shapes.

When a changing current passes through such objects as wire windings or a toroid, it sets up a magnetic field. As the current increases or decreases, the magnetic field strength increase or decreases in the same way. This fluctuation of the magnetic field causes an effect known as inductance, which tends to oppose any further change in current. Inductance (L) in a coil wound around a core is dependant on the number of turns (N), the cross-sectional area of the core (A), the magnetic permeability of the core ($\mu$), and length of the coil (l) according to equation 1 below:

$$L = \frac{0.4\pi N^2 A\mu}{l}. \qquad \text{Equation 1}$$

Figure 3A:
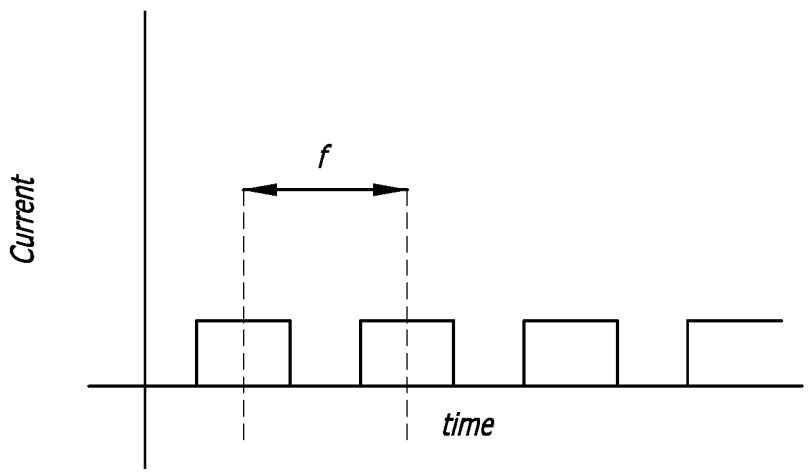
FIG. 3A illustrates example direct signaling current according to the present invention.
Figure 3B:
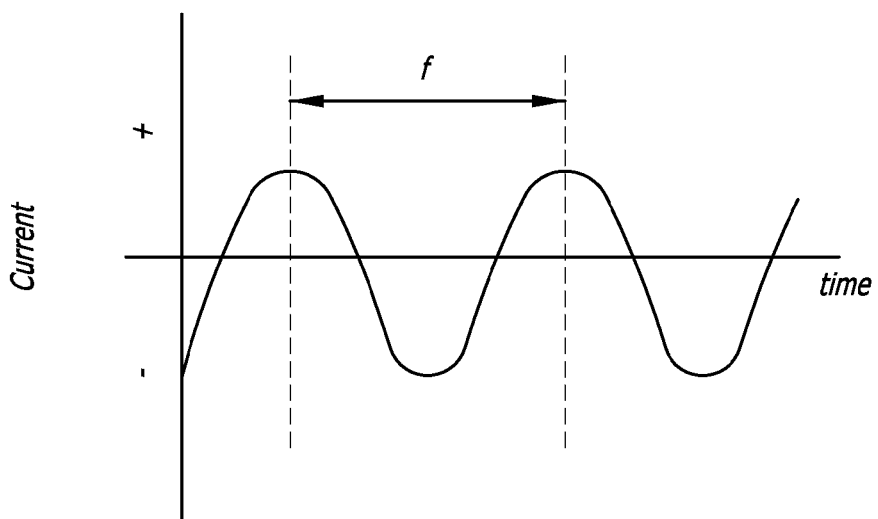
FIG. 3B illustrates example alternating signaling current according to the present invention.

The heater 106 or 306 is formed from a wound coil with proximal and distal electrically conductive wires 108, 110, 308, or 309 attached to a power source. The tether 104, 310 has a magnetic permeability $\mu_1$ and is positioned through the center of the resistive heater, having a length l, cross sectional area A, and N winds, forming a core as described in the previous equation. Prior to detachment, a changing signaling current $i_1$, such as the waveforms shown in FIGS. 3A and 3B, with frequency $f_1$, is sent through the coil windings. This signaling current is generally insufficient to detach the implant. Based on the signaling current, the inductive resistance $X_L$ (i.e. the electrical resistance due to the inductance within the system) is measured by an electronic circuit such as an ohmmeter. The initial inductance of the system $L_1$ is then calculated according to the formula:

$$L_1 = \frac{X_L}{2\pi f_1}. \quad \text{Equation 2}$$

This initial value of the inductance $L_1$ depends on the magnetic permeability $\mu_1$ of the core of the tether 104, 310 according to Equation 1, and is saved for reference. When detachment is desired, a higher current and/or a current with a different frequency than the signaling current is applied through the resistive heater coil, causing the tether 104, 310 to release the implant 112, 302 as previously described. If detachment is successful, the tether 104, 310 will no longer be present within the heater 106, 306 and the inside of the heater 106, 306 will fill with another material such as the patient's blood, contrast media, saline solution, or air. This material now within the heater core will have a magnetic permeability $\mu_2$ that is different than the tether core magnetic permeability $\mu_1$.

A second signaling current and frequency $f_2$ is sent through the heater 106, 306 and is preferably the same as the first signaling current and frequency, although one or both may be different without affecting the operation of the system. Based on the second signaling current, a second inductance $L_2$ is calculated. If the detachment was successful, the second inductance $L_2$ will be different (higher or lower) than the first inductance $L_1$ due to the difference in the core magnetic permeabilities $\mu_1$ and $\mu_2$. If the detachment was unsuccessful, the inductance values should remain relatively similar (with some tolerance for measurement error). Once detachment has been confirmed by comparing the difference between the two inductances, an alarm or signal can be activated to communicate successful detachment to the user. For example, the alarm might include a beep or an indicator light.

Preferably, the delivery system 100, 300 used according to this invention connects to a device that automatically measures inductance at desired times, performs required calculations, and signals to the user when the implant device has detached from the delivery catheter. However, it should be understood that part or all of these steps can be manually performed to achieve the same result.

The inductance between the attached and detached states can also preferably be determined without directly calculating the inductance. For example, the inductive resistance $X_L$ can be measured and compared before and after detachment. In another example, the detachment can be determined by measuring and comparing the time constant of the system, which is the time required for the current to reach a predetermined percentage of its nominal value. Since the time constant depends on the inductance, a change in the time constant would similarly indicate a change in inductance.

The present invention may also include a feedback algorithm that is used in conjunction with the detachment detection described above. For example, the algorithm automatically increases the detachment voltage or current automatically after the prior attempt fails to detach the implant device. This cycle of measurement, attempted detachment, measurement, and increased detachment voltage/current continues until detachment is detected or a predetermined current or voltage limit is attained. In this respect, a low power detachment could be first attempted, followed automatically by increased power or time until detachment has occurred. Thus, battery life for a mechanism providing the detachment power is increased while the average coil detachment time is greatly reduced.

Referring now to FIGS. 9 and 10, there is shown an embodiment of an implant delivery system 500 of the present invention. The implant delivery system 500 and connector system 501 are generally similar to the delivery pusher 301 and connector system 400, respectively, previously described in this application and shown in FIGS. 4 and 6. However, the implant delivery system 500 preferably includes a sensor 502 for detecting when the implant device 302 has been advanced out of a microcatheter 506 to a desired detachment location.

Generally, detachment of the implant device 302 is preferred once the implant device 302 has fully exited the microcatheter 506. In this respect, the sensor 502 is positioned proximal to the implant device 302 on the pusher 301. The sensor 502 detects a change in its environment (i.e., from a location within the microcatheter 506 to a location outside the microcatheter 506, within vasculature of a patient) which is conveyed along wires 504 to the connector system 501 and ultimately to a human interface or display device (not shown) near the user. Preferably, the human interface may include a meter, electronic display, audible tone, or the like.

In yet another preferred embodiment not shown in the figures, the implant device 302 is utilized as a detection mechanism instead of or in addition to the sensor 502. During navigation of the pusher 500 to the target deployment site within the vasculature, the pusher 500 remains within the microcatheter 506 and the coil of the implant device 302 remains relatively straight, as it is confined by the walls defining the internal lumen of the microcatheter 506. When the implant assembly is deployed, the coil of the implant device 302 returns to a curved configuration. The relative resistance of the coil of the implant device 302 from its distal end to its proximal end changes as the coil changes from a straight to a coiled configuration. Thus, the change in resistance can be used as a location detection mechanism.

In one preferred embodiment, the sensor 502 may be a temperature sensor, detecting the temperature differential (e.g., a change from a normal or unbiased state) between the inside and outside of the microcatheter 506. Due to the relatively short period of time during which the microcatheter 506 is disposed within the vasculature, the internal temperature of the microcatheter 506 is typically cooler than the temperature of the vasculature. Hence, the temperature increases markedly as the sensor 502 reaches the detachment zone (i.e., a position of preferred detachment) just outside the microcatheter 506. This jump in temperature is thus used as an indication that the detachment zone has been reached during the advancement of the implant device 302.

In another preferred embodiment, the sensor 502 is a pressure sensor for detecting a pressure differential (e.g., a change from a normal or unbiased state) inside and outside of the microcatheter 506. The pressure inside the microcatheter 506 is relatively constant, whereas the pressure outside the microcatheter 506 varies with systole and diastole of the blood stream. Hence, the sudden change of pressure from a relatively static reading to a dynamic reading can be used as an indication that the implant device 302 has been advanced to the detachment zone.

In another preferred embodiment, the sensor 502 includes both an ultrasound transceiver and sensor for detecting an ultrasound differential (e.g., a change from a normal or unbiased state) between an inside and outside of the microcatheter 506. The ultrasonic transceiver sends ultrasonic waves and receives echoes of the waves in order to determine distances to objects surrounding the transceiver. The walls of the microcatheter are much closer to the transceiver than the walls of the vasculature. Hence, the sudden increase in distance measured by the transceiver can be used as an indication that the implant device 302 has been advanced to the desired detachment zone.

Other sensors capable of detecting differential characteristics between an inside and outside of a microcatheter 506 may also be used.

In another preferred embodiment, the heater coil 306 may serve as a sensor instead of or in addition to sensor 502. A resistance differential (e.g., a change from a normal or unbiased state) of the heater coil 306 may be measured as it is advanced through the microcatheter 506. As the heater coil 502 exits the microcatheter 506, the environment surrounding the heater coil changes from dry and relatively cool, to the warm blood filled environment of the vasculature. This change in environment affects the resistance of the heater coil 306 to a measurable degree. The following example is provided to show data obtained using the heater coil 306 as a sensor:

Examples

A series of experiments were conducted to determine the resistance change of heater coils as they are advanced through a microcatheter. The procedure used in order to obtain the data was as follows:
1. Obtain coil pusher
2. Prepare flow model.
3. Measure and record coil resistance on gold connector.
4. Advance coil pusher into microcatheter slightly beyond hub at proximal end.
5. Measure and record coil resistance. Mark data as 0% pusher length.
6. Advance coil pusher roughly 50% of entire length. Measure and record coil resistance. Mark data as 50% pusher length.
7. Repeat step 6 for 75% and 100% of pusher length, 100% being defined as the detachment zone exiting the distal end of the microcatheter.
8. Retract pusher and stop at above steps (75%, 50%, and 0%) and measure and record data.
9. Repeat cycle 3 times.
10. Measure and record coil pusher resistance one last time in air, outside of the microcatheter.
11. Detach implant and record results.

The following data were collected using various catheter types and heater coil materials. All resistance values shown in Tables 1-3 are in Ohms. Blank values indicate no data was obtained. Percent pusher length is defined as percentage of the pusher inserted into microcatheter, e.g. 100 percent equals detachment coil exited from distal end of microcatheter. Resistance was measured from gold connectors at proximal end of pusher.

As a result of this data, a conclusion was drawn that of the two heater coil materials tested, namely Stablohm and platinum, Stablohm had a coefficient of thermal resistivity that is much higher than that of the platinum. Other materials with a higher coefficient of thermal resistivity may be used to provide a higher sensitivity of the reading instrument. Moreover, the data show that there is a difference in the advancing coil resistance of approximately 0.5 ohm for the platinum coil and 0.4 ohm for the stablohm (from 75%-100% mark).

Example 1

The microcatheter used for Example 1 was a Rapid Transit microcatheter. The heater coil material used was Stablohm 710. The flow temperature was 99 degrees F. The heater coil resistance before testing was 42.1 Ohm. The heater coil resistance after the test was not recorded. Table 1 shows the results of Example 1.

TABLE 1

| Percent Pusher Length | Advance Resistance 1 | Advance Resistance 2 | Retract Resistance 1 |
|---|---|---|---|
| 0 | 42.1 | 42.1 | 42.1 |
| 50 | 42.2 | — | 42.2 |
| 75 | 42.5 | 42.5 | — |
| 100 | 42.6 | 42.6 | 42.6 |

Example 2

The microcatheter used for Example 2 was an Excelsior 1018 microcatheter. The heater coil material used was Platinum. The flow temperature was 98.7 degrees F. The heater coil resistance before testing was 40.9 Ohm, and the heater coil resistance after the test was 40.9 Ohm. Table 2 shows the results of Example 2.

TABLE 2

| Percent Pusher Length | Advance Resistance 1 | Advance Resistance 2 | Advance Resistance 3 | Retract Resistance 1 | Retract Resistance 2 | Retract Resistance 3 |
|---|---|---|---|---|---|---|
| 0 | 40.8 | 41.0 | 41.0 | 41.0 | 41.0 | 41.0 |
| 50 | 40.9 | 41.2 | 41.1 | 41.1 | 41.1 | 41.1 |
| 75 | 41.2 | — | 41.3 | — | — | 41.2 |
| 100 | 41.7 | 41.6 | 41.6 | 41.7 | 41.6 | 41.6 |

Example 3

The microcatheter used for Example 3 was an Excelsior SL10 microcatheter. The heater coil material used was Platinum. The flow temperature was 98.6 degrees F. The heater coil resistance before testing was 40.8 Ohm, and the heater coil resistance after the test was 40.7 Ohm. Table 3 shows the results of Example 3.

TABLE 3

| Percent Pusher Length | Advance Resistance 1 | Advance Resistance 2 | Advance Resistance 3 | Retract Resistance 1 | Retract Resistance 2 | Retract Resistance 3 |
|---|---|---|---|---|---|---|
| 0 | 40.8 | 40.9 | 40.8 | 40.9 | 40.8 | 40.7 |
| 50 | 41.0 | 41.0 | 41.0 | 41.0 | 40.9 | 41.0 |
| 75 | 41.1 | 41.2 | 41.2 | 41.2 | 41.1 | 41.2 |
| 100 | 41.6 | 41.6 | 41.7 | 41.6 | 41.6 | 41.7 |

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A system for determining when an implant has advanced out of a microcatheter comprising:
    a microcatheter having a lumen and a distal end;
    a pusher disposed within the lumen of the microcatheter;
    an implant device advanceable through the lumen by the pusher; and
    a sensor system comprising a resistance-type heater coil located within the microcatheter and disposed proximate the implant; the sensor system calibrated to monitor a resistance of the heater coil, determine a resistance change due to blood entering the microcatheter, and signal when the implant has advanced completely out of the distal end of the microcatheter.

2. The system of claim 1, further comprising a human interface device in data-flow communication with the sensor.

3. A system for determining when an implant has advanced out of a microcatheter comprising:
    a microcatheter having a lumen and a distal end;
    a pusher movable through the lumen of the microcatheter;
    an implant device advanceable through said lumen by the pusher; and
    a sensor assembly comprising a resistance-type heater coil disposed near the distal end of the microcatheter; the sensor system configured to measure and monitor for a resistance change due to blood entering the microcatheter, and signal when the implant has advanced entirely out of said distal end of the microcatheter.

4. The system of claim 3, wherein the sensor assembly has been calibrated for use with the pusher.

5. A system for determining when an implant has advanced out of a catheter comprising:
    a catheter having a lumen and a distal end;
    a pusher disposed within the lumen of the catheter;
    said implant advanceable through the lumen by the pusher; and
    a sensor system comprising a resistance-type heater coil disposed proximate the implant and within the catheter; the sensor system calibrated to monitor resistance of the heater coil, determine a resistance change due to blood entering the catheter, and signal when the implant has advanced fully out of the distal end of the catheter.

6. The system of claim 5, wherein the sensor system has been calibrated for use with the pusher.

* * * * *